United States Patent
Shara et al.

(10) Patent No.: US 10,793,823 B2
(45) Date of Patent: Oct. 6, 2020

(54) MICROBIOLOGICAL GROWTH MEDIA AND METHODS OF USING THE SAME

(71) Applicant: Rapid Micro Biosystems, Inc., Lowell, MA (US)

(72) Inventors: Kate Shara, Nashua, NH (US); Julie Schwedock, Arlington, MA (US); Sommer Vogel, Lowell, MA (US)

(73) Assignee: Rapid Micro Biosystems, Inc., Lowell, MA (US)

( * ) Notice: Subject to any disclaimer, the term of this patent is extended or adjusted under 35 U.S.C. 154(b) by 438 days.

(21) Appl. No.: 15/305,789

(22) PCT Filed: Apr. 24, 2015

(86) PCT No.: PCT/US2015/027652
§ 371 (c)(1),
(2) Date: Oct. 21, 2016

(87) PCT Pub. No.: WO2015/164827
PCT Pub. Date: Oct. 29, 2015

(65) Prior Publication Data
US 2017/0044486 A1 Feb. 16, 2017

Related U.S. Application Data

(60) Provisional application No. 61/983,675, filed on Apr. 24, 2014.

(51) Int. Cl.
| | |
|---|---|
| *C12N 1/20* | (2006.01) |
| *C12N 1/14* | (2006.01) |
| *C12Q 1/04* | (2006.01) |
| *C12N 1/38* | (2006.01) |
| *C12N 1/16* | (2006.01) |

(52) U.S. Cl.
CPC ............. *C12N 1/20* (2013.01); *C12N 1/14* (2013.01); *C12N 1/16* (2013.01); *C12N 1/38* (2013.01); *C12Q 1/045* (2013.01)

(58) Field of Classification Search
CPC ... C12N 1/14; C12N 1/16; C12N 1/20; C12N 1/38; C12Q 1/045
See application file for complete search history.

(56) References Cited

U.S. PATENT DOCUMENTS

| | | |
|---|---|---|
| 5,891,709 A | 4/1999 | Stern et al. |
| 7,387,884 B2 | 6/2008 | Suzuki et al. |
| 7,462,487 B2 | 12/2008 | Tsao |
| 8,066,986 B2 | 11/2011 | Porubcan |
| 2004/0137560 A1 | 7/2004 | Suzuki et al. |
| 2005/0101011 A1 | 5/2005 | Tsao |
| 2005/0124062 A1 | 6/2005 | Subirade et al. |
| 2008/0187525 A1 | 8/2008 | Porubcan |

FOREIGN PATENT DOCUMENTS

| | | |
|---|---|---|
| WO | WO-2010129521 A1 | 11/2010 |
| WO | WO-2014/064359 A1 | 5/2014 |

OTHER PUBLICATIONS

The UNC School of Pharmacy Compounding Lab "Buffers and Buffering Capacity" 2 pgs https://pharmlabs.unc.edu/labs/ophthalmics/buffers.htm, available Apr. 11, 2009 via wayback (Year: 2009).*
DSMZ "696. *Streptococcus suis* Medium" 1pg 2007 (Year: 2007).*
Nghia et al. "Human Case of *Streptococcus suis* Serotype 16 Infection" Emerging Infectious Diseases • www.cdc.gov/eid • vol. 14, No. 1, Jan. 2008, pp. 155-157 (Year: 2008).*
NeoGen Corp, "Schaedler Broth (7154)," retrieved from URL: <http://www.neogen.com/acumedia/pdf/ProdInfo/7154_PI.pdf> (2010) (2 pages).
International Search Report for International Patent Application No. PCT/US2015/027652, dated Jul. 13, 2015 (16 pages).
"BBL(TM) Schaedler K-V Agar with 5% Sheep Blood," published Oct. 1, 2006, <http://legacy.bd.com/ds/technicalCenter/inserts/L007409(06)(1006).pdf>, retrieved on Oct. 26, 2017 (3 pages).
Deschler et al., "Evaluation of the new OxyPlate(TM) Anaerobic System for the isolation of ocular anaerobic bacteria," Int J Opthalmol. 5(5):582-5 (2012).
Eley et al., "Comparative growth of bacteroides species in various anaerobic culture media," J Med Microbiol. 19(2):195-201 (1985).
Rousseau et al., "Prebiotic effects of oligosaccharides on selected vaginal lactobacilli and pathogenic microorganisms," Anaerobe. 11(3):145-53 (2005).
Sheppard et al., "Comparison of different medium bases for the semiquantitative isolation of anaerobes from vaginal secretions," J Clin Microbiol. 28(3):455-7 (1990).
Supplementary European Search Report for European Patent Application No. 15782801.3, dated Oct. 27, 2017 (12 pages).
Hartman et al., Chapter 8: Media and Methods for Isolation and Enumeration of the Enterococci. Advances in Applied Microbiology vol. 8, Wayne Umbreit & D. Perlman, 253-89 (1966).
Becton, Dickinson, and Company, "BBL(TM) CDC anaerobe 5% sheep blood agar with phenylethyl alcohol (PEA)", https://www.bd.com/europe/regulatory/Assets/IFU/US/L007359(08)(1206).pdf, published on Dec. 8, 2006, retrieved on Feb. 19, 2020 (4 pages).
*Microbiology* (vol. 1). Baifukan Co. Ltd., 26-28 (1989) (4 pages).
Remel, "Anaerobic blood agar (CDC) w/ and w/o additives," https://assets.thermofisher.com/TFS-Assets/LSG/manuals/IFU1040.pdf, published in 2012, retrieved on Feb. 19, 2020 (2 pages).

* cited by examiner

*Primary Examiner* — Thane Underdahl
(74) *Attorney, Agent, or Firm* — Clark & Elbing LLP

(57) ABSTRACT

The present invention features general-purpose microbiological growth media capable of supporting growth of microorganisms on membranes. The media contain casein digest, soybean digest, animal tissue digest, yeast extract, dextrose, a phosphate buffer, hemin, and L-cystine. The invention features an all-purpose microbiological growth media that can support the growth of anaerobes, molds, injured spores, and general aerobic bacteria to a greater extent than other media.

33 Claims, 7 Drawing Sheets

MICROBIOLOGICAL GROWTH MEDIA AND METHODS OF USING THE SAME

STATEMENT REGARDING FEDERALLY SPONSORED RESEARCH

This invention was made with Government support under HHSO100201000056C awarded by the Department of Health and Human Services. The Government has certain rights in the invention.

FIELD OF THE INVENTION

In general, the present invention relates to microbiological growth media and methods of their use.

BACKGROUND

In many industries, particularly the food, beverage, healthcare, electronic, and pharmaceutical industries, it is essential to analyze samples for the degree of contamination by microorganisms, such as bacteria, yeasts, or molds rapidly. In particular, pharmaceutical and biologics companies are required to test sterile products for the presence of microbiological contaminants. The traditional test, as described in the United States Pharmacopeia monograph <71>, is a growth-based assay that uses trypticase soy broth (TSB) at 22.5° C. and fluid thioglycollate medium (FTM) at 32.5° C. TSB is a general purpose growth medium, used to detect yeasts, molds, and aerobic bacteria. FTM has aerobic and anaerobic layers and is used to detect obligate anaerobes as well as aerobic bacteria. The intent for this combination of growth conditions is to grow as many organisms as possible. While FTM has the ability to grow anaerobes, it is a poor general purpose medium with limited growth promotion properties for many species. In addition, FTM has a limited ability to support the growth of microorganisms on a surface, particularly, of anaerobic organisms.

Other known growth media, such as Schaedler media, are specialized to support growth of certain microorganisms. For example, Schaedler media are optimized to support growth of human pathogens, whereas testing sterile products requires general media capable of supporting growth of as many microorganisms as possible.

There remains a need for a general growth medium that is capable of supporting growth of aerobic and anaerobic bacteria, in particular, on membranes.

SUMMARY OF THE INVENTION

The invention features an all-purpose microbiological growth media that can support the growth of anaerobes, molds, injured spores, and general aerobic bacteria to a greater extent than other media. The invention features a composition containing casein digest, soybean digest, animal tissue digest, yeast extract, dextrose, a phosphate buffer (e.g., potassium phosphate buffer), hemin, and L-cystine.

In a first aspect, the composition is a solid, e.g., a powder, at 22° C. Embodiments of compositions of the first aspect are summarized in Table 1. The amounts are provided in terms of grams of an individual component relative to a kilogram of the total composition, and one skilled in the art will understand that the total amounts of each of the individual components will not exceed 1 kg.

TABLE 1

| Component | $1^{st}$ Range (g/kg) | $2^{nd}$ Range (g/kg) | $3^{rd}$ Range (g/kg) | Non-limiting Example (g/kg) |
|---|---|---|---|---|
| Casein digest | 1-500 | 50-400 | 100-300 | 245.3 |
| Soybean digest | 0.5-300 | 10-200 | 10-100 | 43.8 |
| Animal tissue digest | 1-500 | 50-400 | 100-300 | 219 |
| Yeast extract | 1-500 | 50-400 | 100-300 | 219 |
| Dextrose | 1-500 | 50-400 | 100-300 | 255 |
| Hemin | 0.1-2 | 0.2-1 | 0.3-0.5 | 0.4 |
| L-cystine | 4-80 | 8-40 | 12-20 | 17.5 |
| SUM: | 1000 | 1000 | 1000 | 1000 |

In particular embodiments of the first aspect, the compositions recited in Table 1 further contain a phosphate buffer, e.g., a mixture of dipotassium hydrogen phosphate or a hydrate thereof and potassium dihydrogen phosphate or a hydrate thereof. In yet other embodiments, the amount of the phosphate buffer, e.g., potassium phosphate buffer, present in the composition of the first aspect is sufficient to provide a buffer capacity of from 0.1 mmol/(pH unit) to 100 mmol/(pH unit), e.g., 1 mmol/(pH unit) to 50 mmol/(pH unit), 2 mmol/(pH unit) to 20 mmol/(pH unit), or 3 mmol/(pH unit) to 10 mmol/(pH unit), in a medium generated by dissolution or suspension of the composition of Table 1 and the phosphate buffer in an aqueous medium (e.g., purified water, sheep blood (e.g., defibrinated sheep blood or laked sheep blood), or both). In other embodiments, phosphate buffer, e.g., potassium phosphate buffer, is present in an amount sufficient to produce a pH of 7.3±0.5 in a liquid or gel composition (e.g., pH of 7.3±0.2).

In some embodiments of the first aspect, the composition further contains a gelling agent. When the composition contains the gelling agent, the composition contains between about 10 g/kg and about 800 g/kg, preferably between about 100 g/kg and about 600 g/kg, and more preferably between about 250 g/kg and about 450 g/kg of the gelling agent (e.g., agar) (e.g., about 350 g/kg of a gelling agent). In some embodiments, the gelling agent is agar. In other embodiments, the gelling agent is gellan, sodium alginate, xanthan gum, guar gum, polyacrylamide, or Eladium™.

In certain embodiments of the first aspect, the composition further contains a surfactant. The composition of the first aspect can contain between about 0 g/kg and about 190 g/kg of the surfactant, e.g., between about 1 g/kg and about 60 g/kg, between about 4 g/kg and about 40 g/kg, or about 20 g/kg of the composition shown in Table 1. The surfactant is preferably a polysorbate (e.g., polysorbate 20, also known as Tween® 20).

In a second aspect, the composition is a liquid at 22° C., and, in a third aspect, the composition is a gel at 22° C. The liquid or gel will include sufficient water or other aqueous solution or suspension to form the liquid or gel. In some embodiments, the liquid or gel composition has a pH of 7.3±0.5 (e.g., pH of 7.3±0.2).

Examples of compositions of the second or a third aspect are provided in Table 2. The amounts are provided in terms of grams of an individual component relative to a kilogram of the total composition (including solvent and gelling agent, if present), and one skilled in the art will understand that the total amounts of all components will not exceed 1 kg.

TABLE 2

| Component | 1st Range (g/kg)[1] | 2nd Range (g/kg) | 3rd Range (g/kg) | Non-limiting Example (g/kg) |
|---|---|---|---|---|
| Casein digest | 0.1-50 | 1-20 | 2-10 | 5.6 |
| Soybean digest | 0.05-30 | 0.1-10 | 0.2-3 | 1 |
| Animal tissue digest | 0.1-50 | 1-20 | 2-10 | 5 |
| Yeast extract | 0.1-50 | 1-20 | 2-10 | 5 |
| Dextrose | 0.1-50 | 1-20 | 2-10 | 5.8 |
| Surfactant | 0-19 | 0.05-5 | 0.1-1 | 0.5 |
| Hemin | 0.005-0.015 | 0.007-0.012 | 0.009-0.011 | 0.01 |
| L-cystine | 0.01-0.5 | 0.01-0.5 | 0.01-0.5 | 0.4 |

In certain embodiments, the composition of the second or third aspect contains from 5 g to 100 g of the composition of Table 1 per kilogram of aqueous medium (e.g., purified water, sheep blood (e.g., defibrinated sheep blood or laked sheep blood), or both), e.g., from 10 g to 50 g, from 20 g to 30 g, or about 23 g of the composition in Table 1.

In other embodiments of the second or third aspect, the compositions recited in Table 2 further contain a phosphate buffer, e.g., potassium phosphate buffer. In yet other embodiments, the amount of the phosphate buffer, e.g., potassium phosphate buffer, present in the composition of the second or third aspect is sufficient to provide a buffer capacity of from 0.1 mmol/(pH unit) to 100 mmol/(pH unit), e.g., 1 mmol/(pH unit) to 50 mmol/(pH unit), 2 mmol/(pH unit) to 20 mmol/(pH unit), or 3 mmol/(pH unit) to 10 mmol/(pH unit).

In particular embodiments of the second or third aspect, the composition further contains sheep blood (e.g., defibrinated sheep blood or laked sheep blood). The concentration of sheep blood in the composition may be less than about 200 mL/kg, and preferably less than about 100 mL/kg (e.g., about 50 mL/kg). In particular embodiments, red blood cells in the sheep blood are lysed (e.g., laked sheep blood or defibrinated sheep blood treated to lyse red blood cells).

In particular embodiments of the second or third aspect, the composition further contains a surfactant. The composition of the second or third aspect can contain between 0 g/kg and 19 g/kg of the surfactant, e.g., between about 0.05 g/kg and about 6 g/kg, between about 0.1 g/kg and about 4 g/kg, or about 0.5 g/kg of the composition shown in Table 2. The surfactant is preferably a polysorbate (e.g., polysorbate 20, also known as Tween® 20).

In certain embodiments of the second aspect and in the third aspect, the composition contains a gelling agent. It will be understood that a liquid may include a gelling agent in an amount insufficient to gel. Examples of gelling agents include agar, gellan, sodium alginate, xanthan gum, guar gum, polyacrylamide, and Eladium™. The concentration of agar or Eladium™ in the composition is, for example, between about 5 g/kg and about 25 g/kg (e.g., about 13.5 g/kg); the concentration of gellan in the composition is, for example, between about 1.0 g/kg and about 13 g/kg (e.g., about 6.8 g/kg; the concentration of xanthan gum or sodium alginate in the composition is, for example, between about 3.4 g/kg and about 17 g/kg (e.g., about 9 g/kg); the concentration of polyacrylamide in said composition is, for example, between about 50 g/kg and about 200 g/kg (e.g., about 150 g/kg); and the concentration of guar gum in said composition is, for example, between about 10 g/kg and about 40 g/kg (e.g., about 21 g/kg).

In certain embodiments of the first through third aspects, the culture medium may further include an antibiotic, e.g., for susceptibility or resistance testing or for selection of resistant cells. In other embodiments of the first through third aspects, the growth medium further includes a disinfectant neutralizer. Examples of disinfectants to be neutralized include alcohols, hypochlorite, hydrogen peroxide, acetic acid, peroxyacetic acid, quaternary ammonium compounds, phenolics, iodine, chlorine preparations, mercurials, formaldehyde, and glutaraldehyde. Examples of neutralizers include histidine, thiosulfate, polysorbate 80, and/or lecithin. Other neutralizers includes bisulfite, glycine, divalent cations (e.g., $Mg^{2+}$ or $Ca^{2+}$), and thioglycollate.

In a fourth aspect, the invention features a method of culturing a population of cells by contacting the population of cells with the composition according to the second or third aspect of the invention under conditions supportive of growth of the population of cells.

In some embodiments of the fourth aspect, the population of cells is disposed on one side of a permeable membrane with the other side of the permeable membrane being in contact with the composition according to the second or third aspect of the invention. Permeable membranes will be porous or otherwise capable of allowing transport of growth medium from one side to the other.

In certain embodiments of the fourth aspect, the population of cells includes aerobes. In other embodiments, the population of cells includes anaerobes (e.g., an obligate anaerobe). In particular embodiments of the fourth aspect, the population of cells include cells belonging to a genus selected from the group consisting of *Acinetobacter* (e.g., *Acinetobacter lwofii*), *Aspergillus* (e.g., *Aspergillus brasiliensis* or *Aspergillus fumigates*), *Bacillus* (e.g., *Bacillus clausii, Bacillus idriensis, Bacillus licheniformis*, or *Bacillus substilis*), *Corynebacterium* (e.g., *Corynebacterium tuberculostearicum* or *Corynebacterium xerosis*), *Dermacoccus* (e.g., *Dermacoccus nishinomiyaensis*), *Escherichia* (e.g., *Escherichia coli*), *Exserohilum* (e.g., *Exserohilum rostratum*), *Kocuria* (e.g., *Kocuria rhizophila*), *Methylobacterium* (e.g., *Methylobacterium radiotolerans*), *Micrococcus* (e.g., *Micrococcus luteus*), *Paenibacillus* (e.g., *Paenibacillus glucanolyticus*), *Penicillium* (e.g., *Penicillium chrysogenum* or *Penicillium notatum*), *Propionibacterium* (e.g., *Propionibacterium acnes*), *Pseudomonas* (e.g., *Pseudomonas aeruginosa*), *Staphylococcus* (e.g., *Staphylococcus aureus, Staphylococcus epidermidis*, or *Staphylococcus hominis*), *Streptococcus* (e.g., *Streptococcus pyogenes*), and *Streptomyces* (e.g., *Streptomyces halstedii*). In some embodiments, the *Bacillus* is oxidatively stressed.

In some embodiments of the fourth aspect, the population of cells is in a sample. The sample may contain fluids or tissues obtained from a multicellular organism (e.g., a bodily fluid or tissue of an animal (e.g., a human or a non-human vertebrate)). The sample may be obtained from the respiratory, urogenital, digestive, or reproductive tract, central nervous system, urine, skin, mucus, blood, plasma, serum, lymph, cerebrospinal fluid, saliva, wound tissue, wound exudate, biopsy, feces, or a solid tissue, or a derivative thereof. In certain embodiments, the sample is a blood or urine sample. The sample can also be derived from a plant or fungus. The sample may be obtained by sampling environmental air, soil, or water, surfaces, objects, or organisms exposed to the environment. The sample may be obtained from raw, finished, or in-process material in the manufacture of pharmaceutical, cosmetic, blood, or other products for topical or internal use in humans or animals; raw, in-process, or finished material in the manufacture of foods, beverages, or nutritional supplements (e.g., vitamins or herbal extracts); raw, in-process, or finished material in the manufacture of medical or in vitro diagnostic devices; chemical products; industrial surfaces; instrumentation; and machinery. The sample may be treated to liquefy and/or homogenize it prior to the contacting step. Additionally or alternatively, prior to the contacting step, the sample may be treated to remove substances or objects other than the population of cells, e.g., by filtration or sedimentation.

In a specific embodiment, the method is a sterility test that contacts the sample with three separate aliquots of the culture medium, one incubated aerobically at room temperature, e.g., about 22° C., one incubated aerobically at an elevated temperature, e.g., about 32.5° C., and one incubate anaerobically at an elevated temperature, e.g., about 32.5° C.

In a fifth aspect, the invention features a method of preparing the composition according to the second aspect of the invention. The method involves:
 i) autoclaving a mixture containing purified water, casein digest, soybean digest, a phosphate buffer, dextrose, animal tissue digest, yeast extract, hemin, and L-cystine;
 ii) optionally cooling the mixture to room temperature;
 iii) optionally adjusting pH to 7.3±0.2 by adding sterile potassium hydroxide or hydrogen chloride to the mixture; and
 iv) adding sheep blood to the mixture.

In some embodiments of the fifth aspect, after step iv), the method further includes step v) holding the temperature of the mixture at about 65° C. until the color of the mixture changes from red to brown (e.g., when sheep blood is defibrinated sheep blood). When laked sheep blood is used, step iv) may occur at or below 45° C.

In particular embodiments of the fifth aspect, the quantities of the ingredients of casein digest, soybean digest, a phosphate buffer, dextrose, animal tissue digest, yeast extract, hem in, and L-cystine are those described in the first aspect of the invention. In certain embodiments of the fifth aspect, the quantity of sheep blood is the same as that described in the second or third aspect of the invention.

In certain embodiments of the fifth aspect, the mixture in step i) further contains a gelling agent, e.g., agar, gellan, sodium alginate, xanthan gum, guar gum, polyacrylamide, or Eladium™.

In some embodiments of the fifth aspect, the mixture in step i) further contains a surfactant, e.g., a polysorbate (e.g., polysorbate 20). Alternatively, the surfactant can be added after step i) (e.g., after step iv) or v)).

In other embodiments of the fifth aspect, the final composition is transferred into a storage vessel (e.g., a bottle, a jar, a vial, an ampoule, or a cassette (e.g., a cassette, such as the cassette described in WO 2013/070730)). The filled sterile storage vessel can be γ-irradiated to sterilize the medium. The dosage of sterilizing γ radiation can be greater than 10 kGy, e.g., between 10 kGy and 50 kGy, between 10 kGy and 40 kGy, between 10 kGy and 30 kGy, or between 10 kGy and 20 kGy (e.g., between 12 kGy and 19 kGy).

In some embodiments of any aspect of the invention, the composition does not contain tris(hydroxymethyl)aminomethane. In particular embodiments of any aspect of the invention, the composition does not include added sodium. For example, none of the dextrose, phosphate buffer, hemin, and L-cystine includes sodium.

In certain other embodiments of any aspect of the invention, the phosphate buffer includes one or more of tripotassium phosphate or a hydrate thereof, dipotassium hydrogen phosphate or a hydrate thereof, and potassium dihydrogen phosphate or a hydrate thereof. In particular embodiments, the phosphate buffer includes one or more of dipotassium hydrogen phosphate or a hydrate thereof and potassium dihydrogen phosphate or a hydrate thereof. In other embodiments, the phosphate buffer is a mixture of dipotassium hydrogen phosphate or a hydrate thereof and potassium dihydrogen phosphate or a hydrate thereof.

In some embodiments of the first aspect of the invention, the composition consists of casein digest, soybean digest, animal tissue digest, yeast extract, dextrose, a phosphate buffer, e.g., potassium phosphate buffer, hemin, L-cystine, and optionally a disinfectant neutralizer. In particular embodiments of the first aspect of the invention, the composition consists of casein digest, soybean digest, animal tissue digest, yeast extract, dextrose, a phosphate buffer, e.g., potassium phosphate buffer, hem in, L-cystine, a gelling agent, and optionally a disinfectant neutralizer. In particular embodiments of the second aspect of the invention, the composition consists of casein digest, soybean digest, animal tissue digest, yeast extract, dextrose, a phosphate buffer, e.g., potassium phosphate buffer, hemin, L-cystine, purified water, and optionally a disinfectant neutralizer. In other embodiments of the second aspect of the invention, the composition consists of casein digest, soybean digest, animal tissue digest, yeast extract, dextrose, a phosphate buffer, e.g., potassium phosphate buffer, hemin, L-cystine, purified water, sheep blood (e.g., defibrinated sheep blood or laked sheep blood), and optionally a disinfectant neutralizer. In other embodiments of the second aspect of the invention, the composition consists of casein digest, soybean digest, animal tissue digest, yeast extract, dextrose, a phosphate buffer, e.g., potassium phosphate buffer, hemin, L-cystine, purified water, sheep blood (e.g., defibrinated sheep blood or laked sheep blood), a surfactant (e.g., polysorbate 20), and optionally a disinfectant neutralizer. In certain embodiments of the third aspect of the invention, the composition consists of casein digest, soybean digest, animal tissue digest, yeast extract, dextrose, a phosphate buffer, e.g., potassium phosphate buffer, hemin, L-cystine, purified water, a gelling agent, and optionally a disinfectant neutralizer. In other embodiments of the third aspect of the invention, the composition consists of casein digest, soybean digest, animal tissue digest, yeast extract, dextrose, a phosphate buffer, e.g., potassium phosphate buffer, hemin, L-cystine, purified water, sheep blood (e.g., defibrinated sheep blood or laked sheep blood), a gelling agent, and optionally a disinfectant neutralizer. In other embodiments of the third aspect of the invention, the composition consists of casein digest, soybean digest, animal tissue digest, yeast extract, dextrose, a phosphate buffer, e.g., potassium phosphate buffer, hemin, L-cystine, purified water, sheep blood (e.g., defibrinated sheep blood or laked sheep blood), a surfactant (e.g., polysorbate 20), a gelling agent, and optionally a disinfectant neutralizer. In any of these embodiments, the disinfectant neutralizer may be omitted. In any of these embodiments, the amounts of the components may be as shown in Table 1 or 2.

The composition of any aspect of the invention may also include a dye or stain, in particular, a stain for live cells, e.g., 5-bromo-4-chloro-3-indolyl-β-D-galactopyranoside (also known as X-Gal; this reagent is an indicator of the presence of a β-lactamase enzyme). This reagent may be used in conjunction with tetrazolium salts (e.g., nitroblue tetrazolium or tetrazolium red). Other dyes that may be used in the compositions of any aspect of the invention include Salmon-Gal, Magenta-Gal, and Green-Gal.

The term "about," as used herein, refers to a value that is ±10% of the recited value.

The term "buffer capacity," as used herein, refers to the number of millimoles of a strong monoprotic acid or a strong monobasic base required to alter the pH of a liquid or a gel composition by 1.0.

The units "g/kg," "mol/kg," and "mL/kg" indicate the ratio of the amount of the ingredient to the total mass of the composition.

The term "purified water," as used herein, refers to water that meets or exceeds the standards for purified water set forth in the *United States Pharmacopeia and National Formulary* (USF 37-NF32), monograph <1231>, 2014.

A composition that is "substantially free of sodium" contains less than 50 g/kg of sodium ions, e.g., less than 10 g/kg or less than 1 g/kg.

DETAILED DESCRIPTION

Growth Media Composition

Figure 1A:
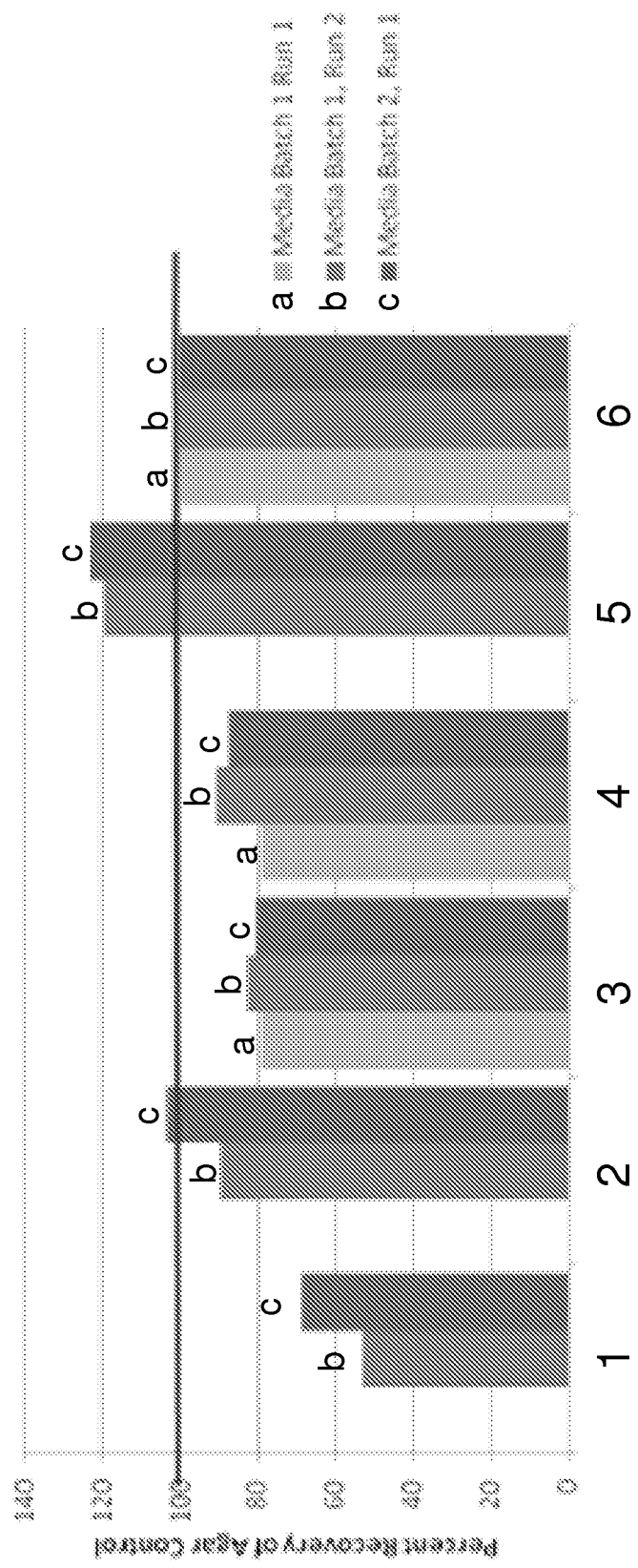
FIG. 1A is a graph of recoveries of bleach-stressed spores of *B. subtilis* in Growth Direct™ Sterility cassettes with different media modifications. The bars labeled (1) represent the data for Schaedler broth prepared according to the original recipe. The bars labeled (2) represent the data for a growth medium prepared according to the original recipe for Schaedler broth but without addition of tris(hydroxymethyl)aminomethane. The bars labeled (3) represent the data for a growth medium prepared according to the original recipe for Schaedler broth but without addition of sodium chloride. The bars labeled (4) represent the data for a growth medium prepared according to the original recipe for Schaedler broth but with addition of a potassium source. The bars labeled (5) represent the data for the growth media of the invention. The bars labeled (6) represent the data for Schaedler chocolate agar medium. The data were normalized to the observed recoveries on Schaedler chocolate agar.

The invention provides an improved growth medium that promotes that growth of a wide variety of organisms from many genera, including human-associated organisms, anaerobes, water organisms, environmental organisms, and molds. Accordingly, the medium may be used as a general purpose medium for assays and cell culture. The versatility of the medium allows it to be used in lieu of trypticase soy broth (TSB) and fluid thioglycollate medium (FTM) in a sterility test. Exemplary fields of use for the growth media of the invention include general cell culture and testing liquid, air, soil, surfaces, industrial or clinical samples, pharmaceutical products (sterile or non-sterile), food products, beverage products, or nutritional supplements for microbial bioburden. The growth medium may also be employed in other assays, such as clinical assays, e.g., for blood or other infections, and assays for antibiotic resistance. The invention features a composition containing casein digest, soybean digest, animal tissue digest, yeast extract, dextrose, phosphate buffer, hemin, and L-cystine. The composition may be a solid, which may be mixed with a liquid (e.g., water and/or sheep blood (e.g., defibrinated sheep blood or laked sheep blood)) to prepare the growth media of the invention according to the methods of the invention. Compositions may also include a surfactant. Preferably, the composition does not contain tris(hydroxymethyl)aminomethane and/or added sodium. The composition is not sodium-free, as the biologically-derived ingredients may contain sodium. This composition of the invention is advantageous as low-sodium content provides superior growth of oxidatively-stressed *B. subtilis*, as compared to the growth of the same on Schaedler broth. In addition, higher potassium content, e.g., from use of potassium phosphate buffer rather than Tris, led to superior growth of, e.g., oxidatively-stressed *B. subtilis*, as compared to the growth of the same on Schaedler broth.

One of skill in the art can establish the final proportions of one or more of potassium phosphate or a hydrate thereof, potassium hydrogen phosphate or a hydrate thereof, and potassium dihydrogen phosphate or a hydrate thereof in the phosphate buffer through routine calculations, e.g., by using the desired pH value and aqueous $pK_a$ values for the relevant conjugate acids in the Henderson-Hasselbalch equation. A pH of about 7.3 (e.g., 7.3±0.5, such as 7.3±0.2) is desired for the media of the invention.

A non-limiting example of a composition of the invention is provided in Table 3.

TABLE 3

| Ingredient | Quantity |
| --- | --- |
| casein digest | 5.6 g |
| soybean digest | 1 g |
| yeast extract | 5 g |
| animal tissue digest | 5 g |
| dextrose | 5.8 g |
| dipotassium phosphate | 2.5 g |
| monopotassium phosphate | 0.31 g |
| L-cystine | 0.4 g |
| hemin | 0.01 g |

This composition in Table 3 may also contain from about 12 to about 15 g of agar (e.g., about 13.5 g of agar). This composition may further be dissolved or suspended in about 1 L of aqueous medium, e.g., about 950 mL of purified water and about 50 mL of sheep blood (e.g., defibrinated sheep blood or laked sheep blood). The composition may further contain 0.05% (w/v) of polysorbate 20. In a non-limiting example, the composition described in Table 3 is combined with 950 mL of purified water, which can further include 50 mL of sheep blood (e.g., laked), and 10 mL of 5% (w/v) polysorbate 20 solution can be added.

Solid compositions of the invention contain casein digest, soybean digest, animal tissue digest, yeast extract, dextrose, a phosphate buffer, hemin, and L-cystine. Certain solid compositions of the invention contain less than about 60 g/kg (e.g., less than about 55 g/kg or less than about 50 g/kg) of sodium ions. Solid compositions of the invention may also contain a gelling agent. A solid composition of the invention that includes a gelling agent affords a gel upon mixing with water, sheep blood, or both. Non-limiting examples of gelling agents include agar, gellan, sodium alginate, xanthan gum, guar gum, gelatin, agarose, Eladium™ (a polysaccharide produced by *Rhizobium* sp. (CNCM number: I-1809)), and combinations thereof. One of skill in the art can determine the quantity of a liquid (e.g., purified water and/or sheep blood) that is required for the preparation of a gel suitable for use as a growth medium. The amount of the gelling agent in the solid composition of the invention depends on the identity of the gelling agent. For example, when the gelling agent present in the dry solid of the invention is gellan, its concentration can be between about 50 g/kg and about 300 g/kg, and preferably between about 130 g/kg and about 230 g/kg (e.g., about 180 g/kg). When the gelling agent present in the gel or liquid of the invention is gellan, its concentration can be between about 2.5 g/kg and about 13 g/kg (e.g., about 6.8 g/kg). In another example, when the gelling agent present in the dry solid of the invention is xanthan gum or sodium alginate, its concentration can be between about 70 g/kg and about 400 g/kg, and preferably between about 160 g/kg and about 300 g/kg (e.g., about 220 g/kg). When the gelling agent present in the gel of the invention is xanthan gum or sodium alginate, its concentration can be between about 3.4 g/kg and about 13 g/kg (e.g., about 6.8 g/kg). In yet another example, when the gelling agent present in the gel of the invention is polyacrylamide, its concentration can be between about 50 g/kg and about 200 g/kg (e.g., about 150 g/kg). In certain examples, when the gelling agent present in the dry solid of the invention is guar gum, its concentration can be between about 400 g/kg and about 800 g/kg (e.g., about 650 g/kg). When the gelling agent present in the gel of the invention is guar gum, its concentration can be between about 10 g/kg and about 40 g/kg (e.g., about 21 g/kg).

Liquid compositions of the invention contain purified water or sheep blood or both. Liquid compositions may also include a gelling agent at a concentration that is too low to form a gel. The concentrations of ingredients in liquid compositions of the invention are as described herein.

Casein digest used in the compositions of the invention can be prepared according to methods known in the art by hydrolysis of casein protein from bovine milk. Soybean digest used in the compositions of the invention can be prepared according to methods known in the art, e.g., through enzymatic digestion of defatted soy flour that was heat-treated to remove heat-labile protease inhibitors. Animal tissue digest used in the compositions of the invention can be prepared according to methods known in the art, e.g., through hydrolysis of meat from muscle tissue or offal and gelatin. Yeast extract is defined in the USP as "a water-soluble, peptone-like derivative of yeast cells ([e.g.,] *Saccharomyces*)" and is readily available as a spray-dried powder. Commercially available casein digest, soybean digest, animal tissue digest, and yeast extract may be used in the compositions of the invention. These ingredients may be obtained, e.g., from BD Biosciences (San Jose, Calif.). Each of these ingredients contains less than 15% (w/w) of sodium.

Defibrinated sheep blood can be prepared according to methods known in the art by aseptic collection of blood from sheep and subsequent mechanical removal of fibrin during the clotting process of the collected blood in the absence of anticoagulants. Commercially available defibrinated sheep blood (e.g., from Rockland Immunochemicals Inc., Gilbertsville, Pa.) may be used in the compositions of the invention. Sheep blood is known to contain sodium (up to 3.48±0.02 g/100 mL; see, e.g., Long et al., *J. Anim. Sci.*, 24:145-150, 1965). Laked sheep blood can be prepared by hemolysis of the defibrinated sheep blood. Commercially available laked sheep blood can be used in the compositions of the invention (e.g., from Cedarlane, Burlington, N.C.).

Surfactants (e.g., nonionic surfactants) can be used in compositions of the invention to control sediment formation in liquid and gel compositions of the invention. The surfactants can be a Poloxamer, a Polysorbate, or a Triton™. These surfactants are commercially available from various chemical suppliers, such as Dow Chemical, Midland, Mich., and Sigma Aldrich, St. Louis, Mo. A preferred surfactant is polysorbate 20.

The growth media of the invention may also include an antibiotic, as is known in the art. The growth medium may further include a disinfectant neutralizer. Examples of disinfectants to be neutralized include alcohols, hypochlorite, hydrogen peroxide, acetic acid, peroxyacetic acid, quaternary ammonium compounds, phenolics, iodine, chlorine preparations, mercurials, formaldehyde, and glutaraldehyde. Examples of neutralizers include histidine, thiosulfate, polysorbate 80, and/or lecithin. Other neutralizers includes bisulfite, glycine, divalent cations (e.g., $Mg^{2+}$ or $Ca^{2+}$), and thioglycollate. As described above, the compositions of the invention preferably include non-biologically derived ingredients that are substantially free of sodium, i.e., the compositions of the invention contain less sodium than Schaedler broth. Preferably, the compositions of the invention do not contain tri(hydroxymethyl)aminomethane (Tris). Absence of this ingredient is advantageous, as quality of Tris is subject to lot-to-lot variations that may lead to poor reproducibility of recoveries of microorganisms grown on media containing this ingredient. A phosphate buffer, e.g., a potassium phosphate buffer, is therefore used in the compositions of the invention.

Methods of Culturing a Population of Cells

The growth media of the invention may be employed as a general growth medium for assays and cell culture. The use of the growth media of the invention is particularly advantageous in growth based sterility assays, e.g., involving the use of cell culture devices employing permeable membranes for growth of microorganisms (e.g., bacteria or fungi). Such cell culture devices are described in detail in International Publication Nos. WO 2007/038478, WO 2013/070730, and WO 2013/158666, the disclosures of which are incorporated herein by reference in their entirety. In particular, the growth media of the invention may be used with a Growth Direct™ Sterility cassette according to the methods described in WO 2013/070730. The particular advantages include rapid achievement of reliable sterility test results, thereby allowing for efficient cost control in healthcare and manufacturing.

In particular, the growth media of the invention can be employed in an analog of the compendial test that employs TSA and FTM. For example, the medium can be employed in a set of three assays, one for aerobes incubated at 32.5° C., one for anaerobes incubated at 32.5° C., and one of aerobes incubated at 22° C. Other uses of the growth media include environmental monitoring, bioburden testing, clinical and diagnostic uses, antibiotic resistance testing, and antibiotic selection. For testing antibiotic susceptibility or selecting cells having antibiotic resistance (e.g., after transfection), the growth media may include an antibiotic, as is known in the art.

The use of the growth media of the invention is not limited to the settings involving growth of microorganisms on permeable membranes. For example, the growth media of the invention may be used to culture microorganisms (e.g., bacteria or fungi) in test tubes, Petri plates, Rodac plates, microfluidic cell culture devices (such as those described in, e.g., U.S. Patent Application Publication Nos. 2013/0090268 and 2013/0171679), bioreactors (such as Eppendorf CellGen® bioreactors or those described in, e.g., U.S. Patent Application Publication Nos. 2013/0196375 and 2014/0024105), and other cell culture vessels.

Samples that can be assayed using the growth media of the invention are not limited and include industrial samples (e.g., raw, in-process, or finished material in the manufacture of foods, beverages, or nutritional supplements; raw, in-process, or finished material in the manufacture of medical or in vitro diagnostic devices; chemical products; industrial surfaces; instrumentation; or machinery), pharmaceuticals and reagent used in preparing pharmaceuticals (e.g., raw, finished, or in-process material in the manufacture of pharmacological, cosmetic, blood, or other products for topical or internal use in humans or animals), biological samples, environmental samples (e.g., water samples (such as natural bodies of water (such as rivers, lakes, ponds, and oceans), waste water, and treated sources of water (such as municipal water supplies)), air samples, soil samples, and surface samples). Surfaces that may be tested include equipment, materials, and facilities used in the manufacture, packaging, or storage of goods (e.g., pharmaceuticals); equipment, materials, and facilities used in research; clothing, bedding, and other fabrics (e.g., for medical providers or patients); and equipment, materials, and facilities used in treatment (e.g., hospitals, clinics, and doctor's offices).

The non-limiting examples of the genera of microorganisms (e.g., bacteria or fungi) that can be cultured using the growth media of the invention include *Acinetobacter* (e.g., *Acinetobacter lwofii*), *Aspergillus* (e.g., *Aspergillus brasiliensis* or *Aspergillus fumigates*), *Bacillus* (e.g., *Bacillus clausii*, *Bacillus idriensis*, *Bacillus licheniformis*, or *Bacillus substilis*), *Candida* (e.g., *Candida albicans*), *Clostridium* (e.g., *Clostridium sporogenes*), *Corynebacterium* (e.g., *Corynebacterium tuberculostearicum* or *Corynebacterium xerosis*), *Dermacoccus* (e.g., *Dermacoccus nishinomiyaensis*), *Escherichia* (e.g., *Escherichia coli*), *Exserohilum* (e.g., *Exserohilum rostratum*), *Kocuria* (e.g., *Kocuria rhizophila*), *Methylobacterium* (e.g., *Methylobacterium radiotolerans*), *Micrococcus* (e.g., *Micrococcus luteus*), *Paenibacillus* (e.g., *Paenibacillus glucanolyticus*), *Penicillium* (e.g., *Penicillium chrysogenum* or *Penicillium notatum*), *Pseudomonas* (e.g., *Pseudomonas aeruginosa* or *Pseudomonas fluorescens*), *Sphingomonas* (e.g., *Sphingomonas japonica*), *Staphylococcus* (e.g., *Staphylococcus aureus*, *Staphylococcus epidermidis*, or *Staphylococcus hominis*), *Streptococcus* (e.g., *Streptococcus pyogenes*), and *Streptomyces* (e.g., *Streptomyces halstedii*). In particular, the growth media of the invention allow for reproducibly good recovery of numerous microorganisms, including bleach-stressed *B. subtilis*.

Kits of the Invention

The invention also features kits containing the compositions of the invention described above. The compositions of the invention may be included in the kits of the invention as dry goods, e.g., powders, gels, or liquids. The solids, e.g., powders, may be packaged as a mixture in a single container (e.g., a bottle, an ampoule, or a jar). Alternatively, the solids, e.g., powder, may be packaged in separate containers (e.g., a bag, a can, a pouch, a bottle, a vial, an ampoule, a jar, or a combination thereof). The mixture may contain one or more of casein digest, soybean digest, animal tissue digest, yeast extract, dextrose, a phosphate buffer, hemin, L-cystine, and a gelling agent (e.g., agar, gellan, sodium alginate, xanthan gum, guar gum, gelatin, agarose, Eladium™, or a combination thereof). The relative quantities of these ingredients are as described above.

The following examples are meant to illustrate the invention and are not meant to limit the invention in any way.

EXAMPLES

Example 1

Preparation of Growth Media of the Invention

A composition containing purified water (950 mL), casein digest (5.6 g, Neogen or BD Biosciences), soybean digest (1 g, Neogen), dipotassium phosphate (2.5 g, Sigma-Aldrich), dextrose (5.82 g, Sigma-Aldrich), animal tissue digest (5 g, BD Biosciences or Neogen), yeast extract (5 g, BD Biosciences or Neogen), monopotassium phosphate (0.31 g, Sigma-Aldrich), hemin (0.01 g, Sigma-Aldrich), and L-cystine (0.4 g, Sigma-Aldrich) was autoclaved. The composition was cooled to room temperature, and pH was adjusted to 7.3 (±0.2) using aqueous KOH or HCl. The composition was then heated to 65° C., and 50 mL of defibrinated sheep blood (Northeast Laboratories or Thermo Scientific) was added. The temperature was held constant until the color changed from red to brown, at which time the composition was allowed to cool to ambient temperature (room temperature, about 22° C.).

Example 2

Comparison of Growth of Microorganisms on Various Growth Media

This example illustrates the versatility of the growth media of the invention in supporting the growth of various microorganisms as compared to the standard media used in the growth-based sterility assays described in United States Pharmacopeia monograph <71>. The standard media are TSB and FTM.

The growth media of the invention were tested against a variety of organisms. The media of the invention were also compared to other growth media known in the art. All tests were carried out in Growth Direct™ Sterility cassettes (Rapid Micro Biosystems, Bedford, Mass.) or Petri plates.

Figure 1B:
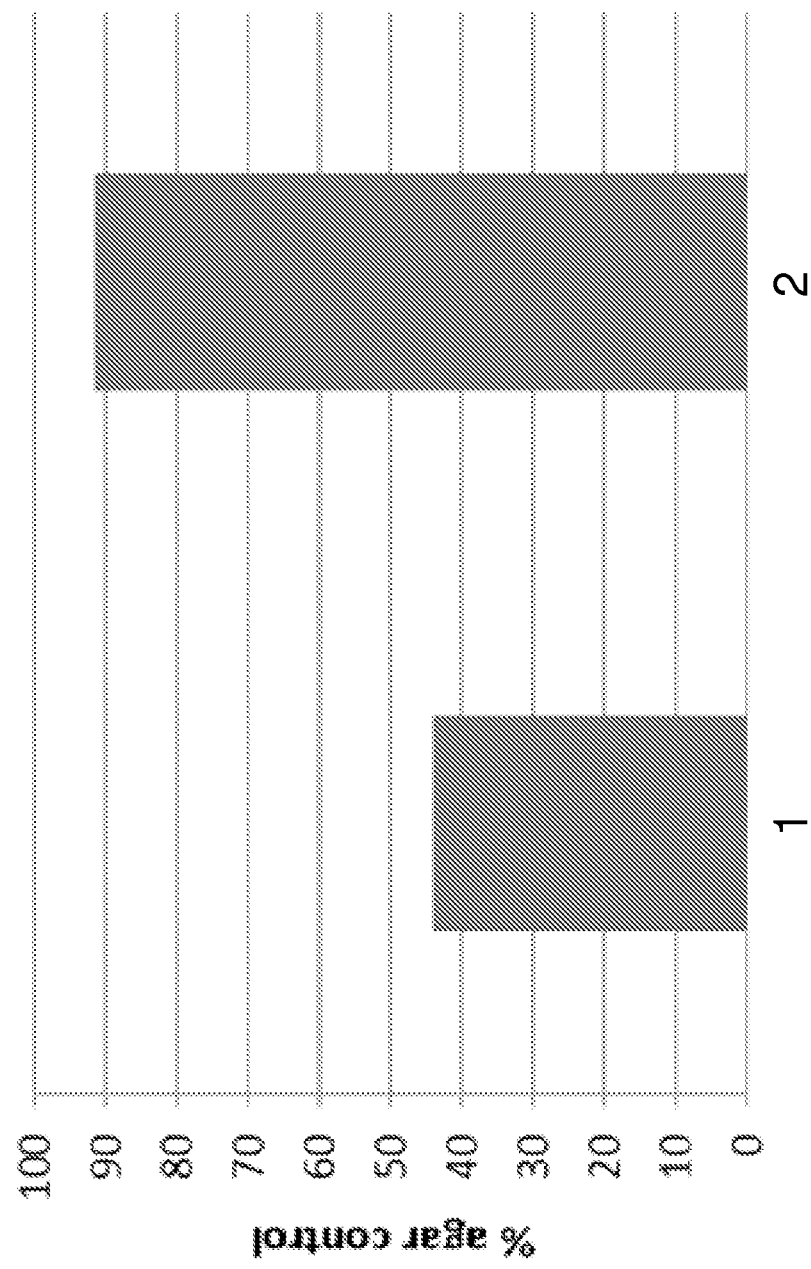
FIG. 1B is a graph of recoveries of bleach-stressed spores of *B. subtilis* in Growth Direct™ Sterility cassettes. The bar labeled (1) represents the data for Schaedler blood broth. The bar labeled (2) represents the data for the growth media of the invention. The grown media were prepared with all new lots of the individual ingredients. The data were normalized to the observed recoveries on Schaedler chocolate agar.

Comparison of Modifications of Schaedler Broth to the Original Recipe, Schaedler Chocolate Agar, and Growth Medium of the Invention The recovery of bleach-stressed *B. subtilis* on Schaedler broth prepared according to the original recipe (1), Schaedler broth without Tris (2), Schaedler broth containing non-biologically-derived ingredients that are substantially free of sodium (3), Schaedler broth that is high in potassium (4), the growth medium of the invention (5), and Schaedler chocolate agar (6) are shown in FIG. 1A. The tests were performed in triplicate with two different batches of each medium. The results were normalized to the recovery on Schaedler chocolate Medium. As shown in FIG. 1B, the results are reproducible, even with different underlying lots of the powdered ingredients and/or blood.

Figure 2:
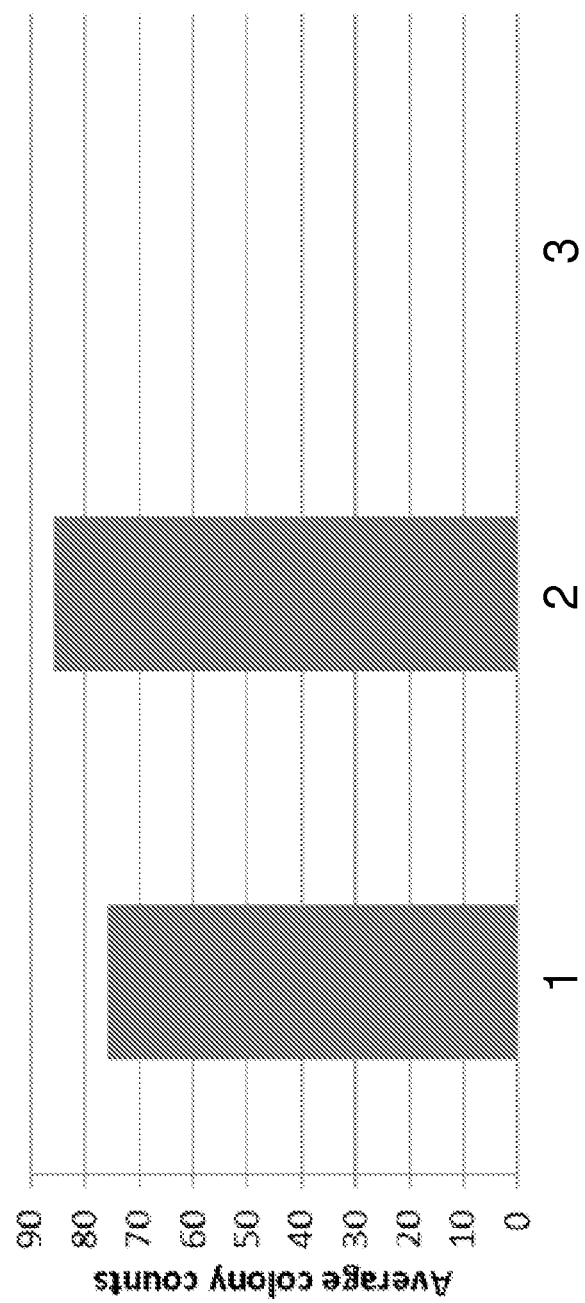
FIG. 2 is a graph of recoveries of *Methylobacterium radiotolerans* in Growth Direct™ Sterility cassettes. The bar labeled (1) represents the data for Schaedler blood broth. The bar labeled (2) represents the data for the growth media of the invention. The data for TSA on Petri plates is labeled (3). The data could not be normalized to the recovery of *M. radiotolerans* from trypticase soy agar on Petri plates, because no growth of *M. radiotolerans* was observed on this medium.

Comparison of the Recovery Using Growth Media of the Invention in Growth Direct™ Sterility Cassettes to the Recovery Using the TSA on Petri Plates The growth of 23 different organisms on growth media of the invention in Growth Direct™ Sterility cassettes was compared to the growth of the same organisms on TSB on Petri plates. The results were normalized to the observed growth on TSA on Petri plates. Only three organisms exhibited recovery below the 70% cutoff (the USP standard) for good growth. For two organisms, *Dermacoccus nishinomiyaensis* and *M. radiotolerans*, growth in the Sterility Cassette on the growth media of the invention was consistently superior. FIG. 2 shows the data for *Methylobacterium radiotolerans*; however, the growth could not be normalized to TSA because no growth was observed on TSA.

Figure 3:
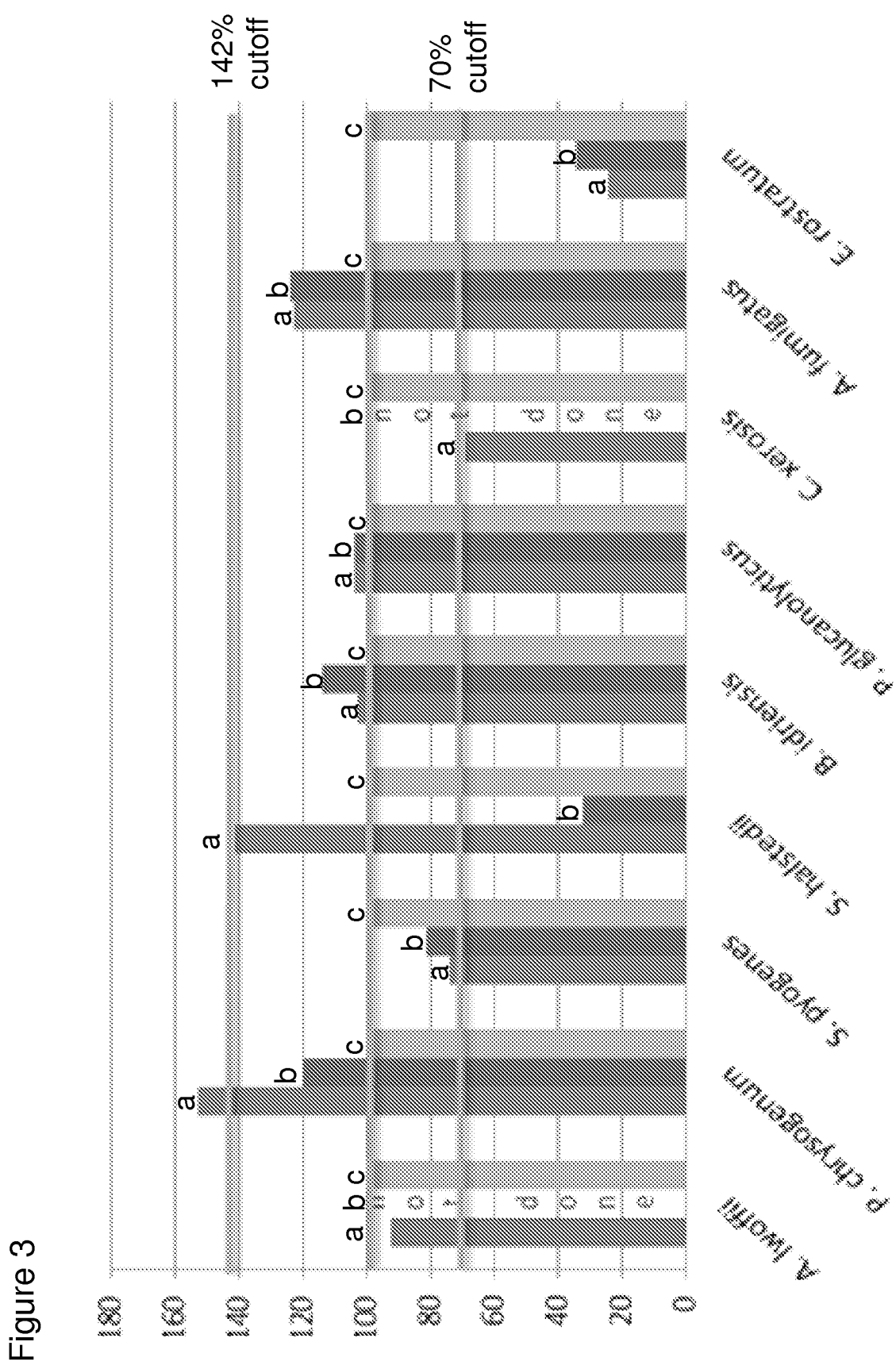
FIG. 3 is a graph of recoveries of nine different microorganisms grown on liquid media. The bars labeled (a) represent the data for TSB. The bars labeled (b) represent the data for Schaedler blood broth. The bars labeled (c) represent the data for the growth media of the invention. The data were normalized to the observed recoveries on the growth media of the invention. The 70% cutoff is shown to indicate inferior growth, as compared to the growth media of the invention. The 142% cutoff is shown to indicate superior growth, as compared to the growth media of the invention. The 142% cutoff was selected, as the ratio of 100% to 142% gives 70%.

Comparison of Growth of Microorganisms in Growth Direct™ Sterility Cassettes Using TSB, Schaedler Blood Broth, and Growth Media of the Invention Growth on different media within the context of the Sterility Cassette was investigated to eliminate the variable of agar. The focus of this study was on problematic organisms. FIG. 3 shows this comparison, with the data normalized to growth on the growth media of the invention. For five organisms, there is no significant difference among all the media. All growth falls between the 70% and 142% cutoffs. For two organisms, *C. xerosis* and *Exserohilum rostratum*, growth is superior on the growth media of the invention. For *S. halstedii* and *P. chrysogenum*, growth on TSB is superior, yet in all cases, growth is detected. No organism was identified that can grow on TSA, TSB, or Schaedler blood or chocolate agar, that cannot grow on growth media of the invention.

Comparison of Growth of Microorganisms on Growth Media of the Invention to the Growth of the Same Microorganisms on FTM FTM is designed for growing anaerobes in a liquid format. The media has both aerobic and anaerobic layers, so it is also meant to be an all-purpose media. Because it is a liquid growth media but does not support growth on the surface of a filtration membrane, growth can only be monitored by the presence of turbidity. The presence/absence nature of this information can be converted to quantitative data using a Most Probable Number (MPN) method, where replicate 10-fold dilutions of low level inocula are monitored for growth, and the pattern of growth/no-growth can be converted to a most probable inoculum for the most concentrated inoculation.

This method was used to compare the growth of *Propionibacterium acnes* in anaerobic sterility cassettes with the growth media of the invention to growth in FTM using MPN method. As shown in Table 4, counts in the anaerobic cassette are similar to those in FTM using MPN method. However, *P. acnes* grew significantly faster on the growth media of the invention compared to growth in FTM.

TABLE 4

Recovery of *Propionibacterium acnes* in Growth Direct ™ cassettes and FTM.

|  | Anaerobic sterility cassette with growth media of the invention | FTM (Most Probable Number analysis) |
| --- | --- | --- |
| Count | 28.2 | 23 |
| Days to detection | <5 days by eye | >7 days by eye |

The growth of some aerobic organisms in FTM was compared to their growth on the growth media of the invention. The focus of this test was on molds, the recoveries of which were observed to be below 70% in Growth Direct™ sterility cassettes with the growth media of the invention when compared to growth on TSA. MPN analysis was performed to obtain quantitative data from the growth/no growth information of FTM. As shown in Table 5, the molds grew very poorly in FTM as compared to their growth on TSA or even Schaedler chocolate agar (SCA). Growth in sterility cassettes on media of the invention was significantly better. (Compare 6$^{th}$ column, % growth in FTM, to last column, % growth in cassettes. Growth was normalized to TSA controls.)

TABLE 5

Recovery of molds TSA, SCA, FTM, and the growth media of the invention

| | 32.5° C. | | | | | 22.5° C. | | | 22.5° C. |
| --- | --- | --- | --- | --- | --- | --- | --- | --- | --- |
| | | | FTM | | | | | | |
| | TSA | SCA | FTM | MPN | % TSA | TSA | SCA | TSB | Cassette |
| *A. brasiliensis* | 17.5 | 11.5 | 1/3 | 0.41 | 2% | 17.5 | 13.0 | 3/3 | 76% |
| *A. fumigates* | 17.0 | 11.5 | 2/3 | 1.1 | 6% | 5.5 | 8.0 | 3/3 | 68% |
| *P. chrysogenum* | 10.5 | 7.5 | 0/3 | <0.41 | <4% | 4.5 | 10.0 | 3/3 | 37% |

Example 3

A growth medium composition containing purified water (950 mL), casein digest (5.6 g), soybean digest (1 g), dipotassium phosphate (2.5 g), dextrose (5.82 g), animal tissue digest (5 g), yeast extract (5 g), monopotassium phosphate (0.31 g), hemin (0.01 g), L-cystine (0.4 g), and laked sheep blood (50 mL) or defibrinated sheep blood (50 mL) having a pH of 7.3±0.2 was employed. The composition containing laked sheep blood was prepared as described in Example 1 with the exception that laked sheep blood was added at 45° C. or cooler to the mixture prepared as described in Example 1.

Membrane filters were placed on broth soaked pads. The growth promotion of the composition was compared to trypticase soy agar (TSA) using a suite of test organisms inclusive of human-associated strains, water organisms, yeast, USP microorganisms, mold and a number of spore-forming *Bacillus* sp. (Table 6). In Table 6, % recovery indicates the recovery of microorganisms on the growth medium of the invention (not containing polysorbate 20) as a percentage of recovery on TSA.

TABLE 6

| Laked or defibrinated blood | Organism | % Recovery |
|---|---|---|
| | Soil Microorganisms | |
| defibrinated blood | *Acinetobacter lwoffii* | 121 |
| defibrinated blood | *Paenibacillus glucanolyticus* | 79 |
| defibrinated blood | *Streptomyces halstedii* | 71 |
| defibrinated blood | *Bacillus clausii* | 106 |
| defibrinated blood | *Bacillus licheniformis* | 100 |
| | Mold Spores | |
| defibrinated blood | *Penicillium notatum* | 83 |
| laked blood | *Penicillium chrysogenum* | 86 |
| | Water Microorganisms | |
| laked blood | *Methylobacterium radiotolerans* | 213 |
| laked blood | *Sphingomonas japonica* | 613 |
| laked blood | *Pseudomonas fluorescens* | 98 |
| | USP Microorganisms | |
| laked blood | *Escherichia coli* | 88 |
| laked blood | *Staphylococcus aureus* | 84 |
| laked blood | *Pseudomonas aeruginosa* | 116 |
| laked blood | *Bacillus subtilis* | 158 |
| laked blood | *Candida albicans* | 113 |
| laked blood | *Aspergillus brasiliensis* | 92 |
| | Human-associated Microorganisms | |
| defibrinated blood | *Staphylococcus epidermidis* | 92 |
| defibrinated blood | *Staphylococcus warnerii* | 96 |
| defibrinated blood | *Staphylococcus hominis* | 104 |
| defibrinated blood | *Staphylococcus capitis* | 177 |
| laked blood | *Staphylococcus haemolyticus* | 115 |
| laked blood | *Corynebacterium xerosis* | 6550 |
| defibrinated blood | *Kocuria rhizophila* | 106 |
| laked blood | *Dermacoccus nishinomiyaensis* | 98 |
| defibrinated blood | *Corynebacterium tuberculostearicum* | 101 |
| defibrinated blood | *Micrococcus luteus* | 110 |
| laked blood | *Streptococcus pyogenes* | 94 |

Figure 4:
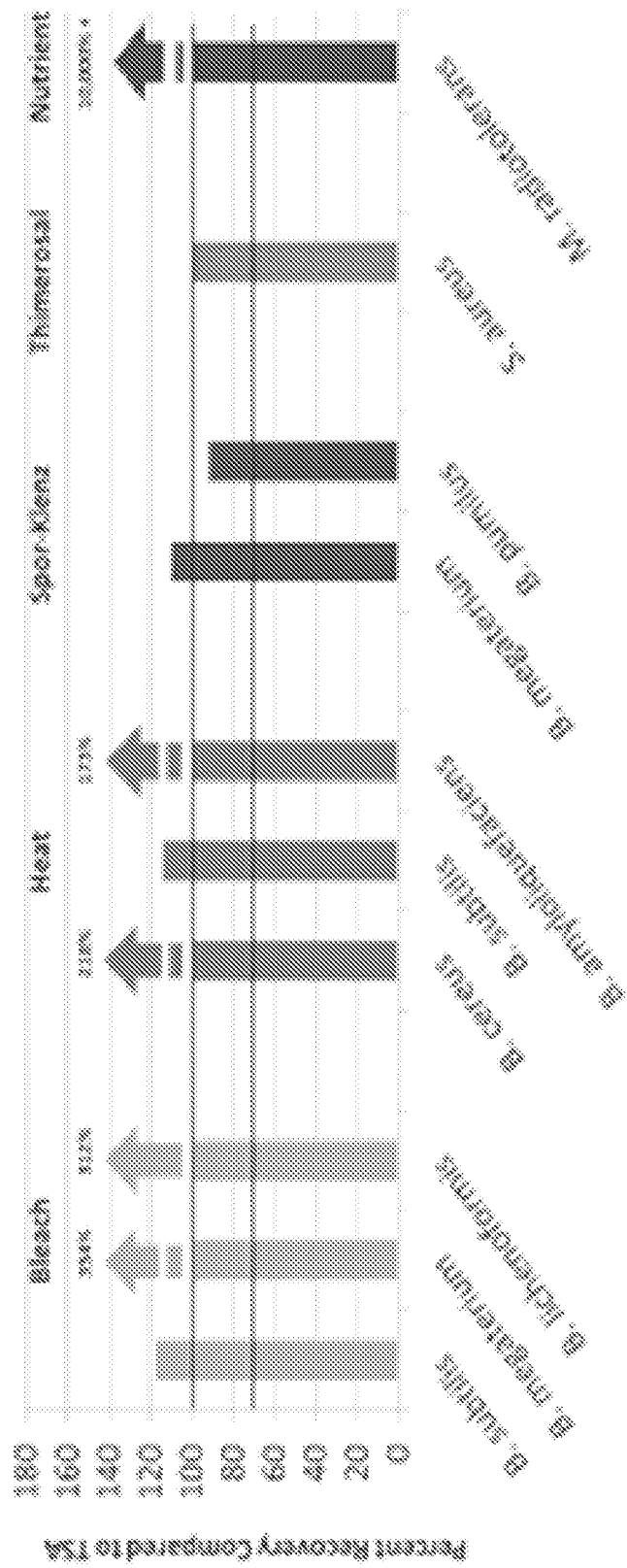
FIG. 4 is a graph of recoveries of ten different stressed microorganisms grown on the growth media of the invention relative to the recoveries of the same on TSA. The stress sources are identified in the figure as bleach, heat, Spor-Klenz® (mixture of hydrogen peroxide, peracetic acid, and acetic acid), thimerosal, and nutrient. The recoveries on the growth medium of the invention are shown in percentages of the recoveries on TSA of the corresponding stressed microorganisms.

Further, recoveries of stressed microorganisms on the growth medium of the invention were compared to the recoveries on TSA by following the procedure described above. As shown in FIG. 4, recoveries of all bleach-stressed, heat-stressed, and nutrient-stressed microorganisms were superior on the growth medium of the invention as compared to TSA. Recoveries of Spor-Klenz®-stressed and thimerosal-stressed microorganisms on the growth medium of the invention were comparable to those on TSA. Growth medium of the invention used in this test was prepared with defibrinated sheep blood and without polysorbate 20.

In all cases, the growth medium of the invention exhibited growth promotion that was comparable or better than TSA across all the strains tested. In no case was recovery of the test strains on the growth medium of the invention substantially inferior to that of TSA.

Figure 5:
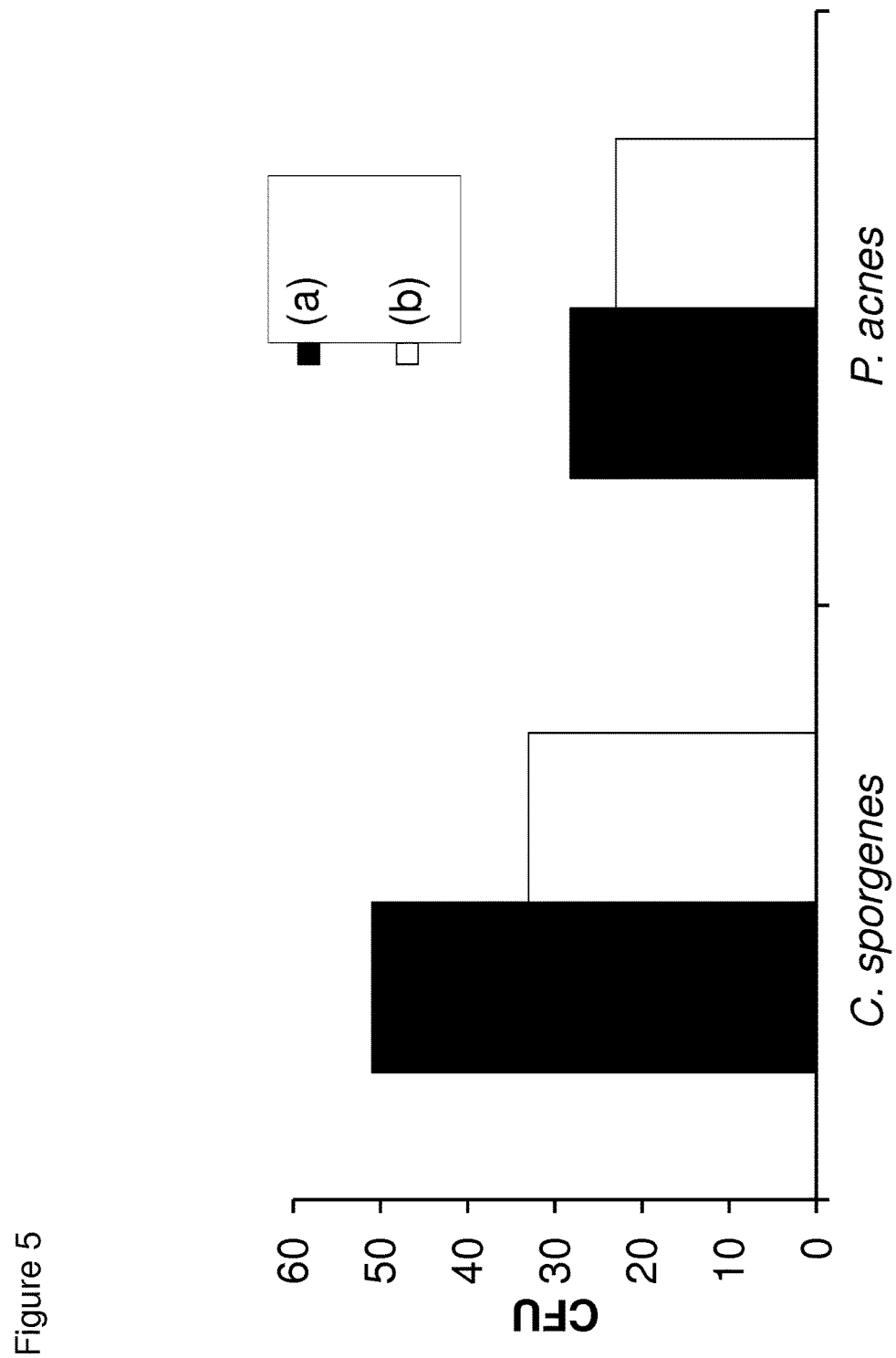
FIG. 5 is a graph showing recoveries of anaerobes *C. sporogenes* and *P. acnes* on the growth medium of the invention (a), as determined by enumeration of colonies, vs. MPN analysis from FTM media.

Additionally, growth of the medium of the invention was compared with calculated MPN from organisms spiked and grown in FTM as described by the compendial sterility test. The anaerobic organisms *P. acnes* and *C. sporogenes* were tested to see if the growth medium of the invention, when under anaerobic conditions, exhibited the same growth promotion as FTM. As shown, both strains exhibited comparable recovery on membrane filters incubated anaerobically on cellulose pads with the growth medium of the invention vs. the MPN obtained from incubation in FTM (FIG. 5).

Example 4

A growth medium composition containing purified water (950 mL), casein digest (5.6 g), soybean digest (1 g), dipotassium phosphate (2.5 g), dextrose (5.82 g), animal tissue digest (5 g), yeast extract (5 g), monopotassium phosphate (0.31 g), hemin (0.01 g), L-cystine (0.4 g), laked sheep blood (50 mL), and 10 mL of 5% (w/v) polysorbate 20 having a pH of 7.3±0.2 was employed. The composition was prepared as described in Example 1 with the exception that laked sheep blood was added at 45° C. or cooler to the mixture prepared as described in Example 1.

Figure 6:
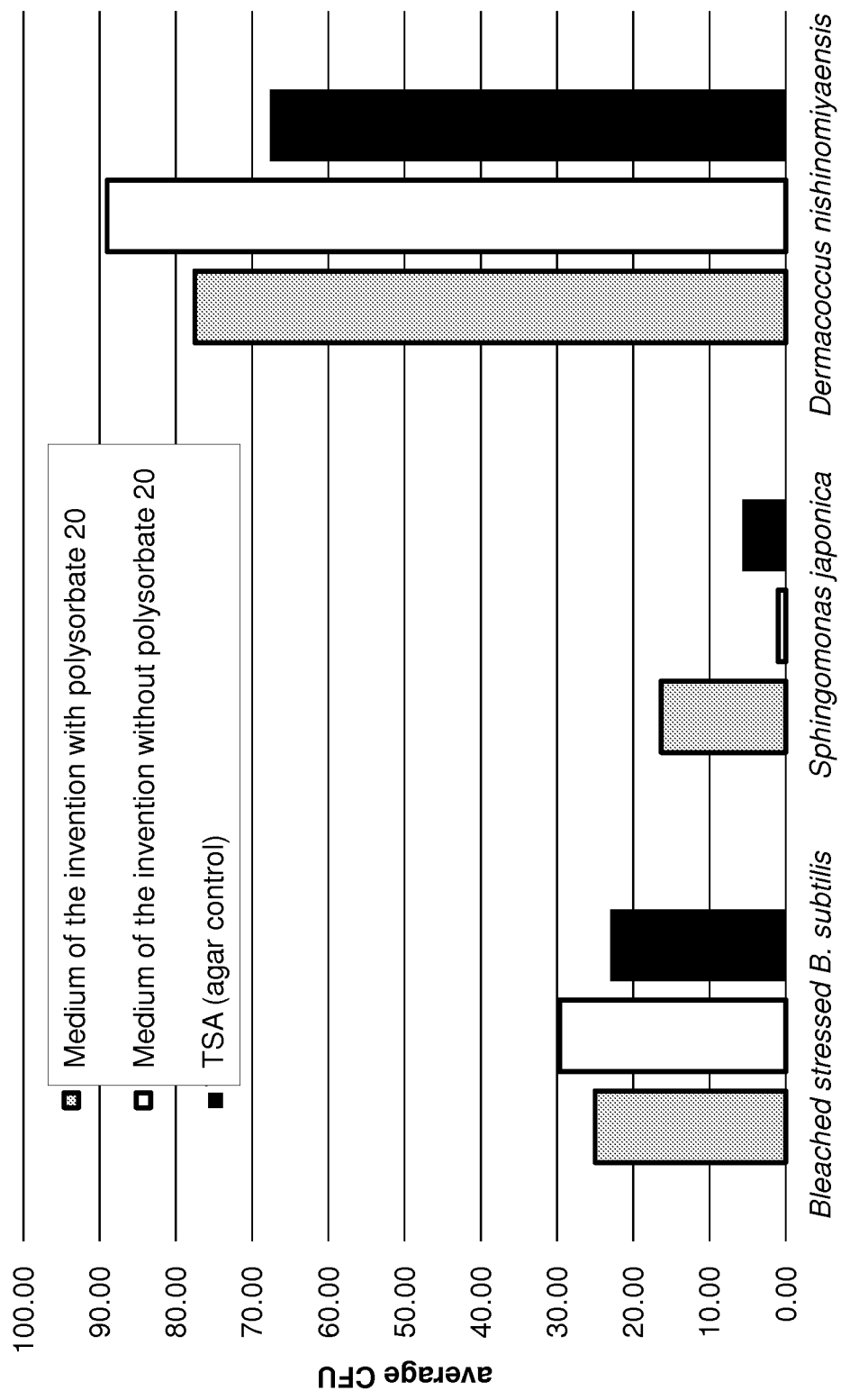
FIG. 6 is a graph showing recoveries of bleach-stressed *B. subtilis, S. japonica,* and *D. nishinomiyaensis* on the growth medium of the invention with (left bar) or without (middle bar) polysorbate 20. The data for the growth medium of the invention are compared to the recoveries of the same microorganisms on TSA.

Growth of bleach-stressed *B. subtilis*, *S. japonica*, and *D. nishinomiyaensis* on the media of the invention containing polysorbate 20 was compared to the growth on the media of the invention free of polysorbate 20 and to the growth on TSA. The results are shown in FIG. 6. The growth medium of the invention containing polysorbate 20 was also tested for its capability of supporting the growth of anaerobes (e.g., *P. acnes*). *P. acnes* were grown on Growth Direct™ anaerobic sterility cassettes using the growth medium of the invention and the recovery was compared to growth on blood agar plates in BD anaerobic GasPak™ pouches. Recovery of *P. acnes* on the growth medium of the invention was 13.2 CFU on average as compared to 18 CFU for blood agar control.

The invention is also described by the following numbered embodiments.

1. A composition comprising casein digest, soybean digest, animal tissue digest, yeast extract, dextrose, a phosphate buffer, hem in, and L-cystine.
2. The composition of embodiment 1, wherein, at 22° C., said composition is solid.
3. The composition of embodiment 2, wherein said composition is a powder.
4. The composition of embodiment 2 or 3, wherein, excluding said phosphate buffer from the total mass of said composition, said composition comprises between about 1 g/kg and about 500 g/kg of casein digest.
5. The composition of embodiment 4, wherein, excluding said phosphate buffer from the total mass of said composition, said composition comprises between about 50 g/kg and about 400 g/kg of casein digest.
6. The composition of embodiment 5, wherein, excluding said phosphate buffer from the total mass of said composition, said composition comprises between about 100 g/kg and about 300 g/kg of casein digest.

7. The composition of embodiment 6, wherein, excluding said phosphate buffer from the total mass of said composition, said composition comprises about 245.3 g/kg of casein digest.
8. The composition of any one of embodiments 2 to 7, wherein, excluding said phosphate buffer from the total mass of said composition, said composition comprises between about 0.5 g/kg and about 300 g/kg of soybean digest.
9. The composition of embodiment 8, wherein said, excluding said phosphate buffer from the total mass of said composition, composition comprises between about 10 g/kg and about 200 g/kg of soybean digest.
10. The composition of embodiment 9, wherein, excluding said phosphate buffer from the total mass of said composition, said composition comprises between about 10 g/kg about 100 g/kg of soybean digest.
11. The composition of embodiment 10, wherein, excluding said phosphate buffer from the total mass of said composition, said composition comprises about 43.8 g/kg of soybean digest.
12. The composition of any one of embodiments 2 to 11, wherein, excluding said phosphate buffer from the total mass of said composition, said composition comprises between about 1 g/kg and about 500 g/kg of animal tissue digest.
13. The composition of embodiment 12, wherein, excluding said phosphate buffer from the total mass of said composition, said composition comprises between about 50 g/kg and about 400 g/kg of animal tissue digest.
14. The composition of embodiment 13, wherein, excluding said phosphate buffer from the total mass of said composition, said composition comprises between about 100 g/kg and about 300 g/kg of animal tissue digest.
15. The composition of embodiment 14, wherein, excluding said phosphate buffer from the total mass of said composition, said composition comprises about 219 g/kg of animal tissue digest.
16. The composition of any one of embodiments 2 to 15, wherein, excluding said phosphate buffer from the total mass of said composition, said composition comprises between about 1 g/kg and about 500 g/kg of yeast extract.
17. The composition of embodiment 16, wherein, excluding said phosphate buffer from the total mass of said composition, said composition comprises between about 50 g/kg and about 400 g/kg of yeast extract.
18. The composition of embodiment 17, wherein, excluding said phosphate buffer from the total mass of said composition, said composition comprises between about 100 g/kg and about 300 g/kg of yeast extract.
19. The composition of embodiment 18, wherein, excluding said phosphate buffer from the total mass of said composition, said composition comprises about 219 g/kg of yeast extract.
20. The composition of any one of embodiments 2 to 19, wherein, excluding said phosphate buffer from the total mass of said composition, said composition comprises between about 1 g/kg and about 500 g/kg of dextrose.
21. The composition of embodiment 20, wherein, excluding said phosphate buffer from the total mass of said composition, said composition comprises between about 50 g/kg and about 400 g/kg of dextrose.
22. The composition of embodiment 21, wherein, excluding said phosphate buffer from the total mass of said composition, said composition comprises between about 100 g/kg and about 300 g/kg of dextrose.
23. The composition of embodiment 22, wherein, excluding said phosphate buffer from the total mass of said composition, said composition comprises about 255 g/kg of dextrose.
24. The composition of any one of embodiments 2 to 23, wherein said composition comprises a quantity of phosphate buffer sufficient to provide a buffer capacity of from 0.1 mmol/(pH unit) to 100 mmol/(pH unit) upon dissolution in an aqueous medium.
25. The composition of embodiment 24, wherein said composition comprises a quantity of phosphate buffer sufficient to provide a buffer capacity of from 1 mmol/(pH unit) to 50 mmol/(pH unit) upon dissolution in an aqueous medium.
26. The composition of embodiment 25, wherein said composition comprises a quantity of phosphate buffer sufficient to provide a buffer capacity of from 2 mmol/(pH unit) to 20 mmol/(pH unit) upon dissolution in an aqueous medium.
27. The composition of embodiment 26, wherein said composition comprises a quantity of phosphate buffer sufficient to provide a buffer capacity of from 3 mmol/(pH unit) to 10 mmol/(pH unit) upon dissolution in an aqueous medium.
28. The composition of any one of embodiments 2 to 27, wherein said composition comprises between about 0.2 g/kg and about 1 g/kg of hemin.
29. The composition of embodiment 28, wherein said composition comprises about 0.4 g/kg of hemin.
30. The composition of any one of embodiments 2 to 29, wherein, excluding said phosphate buffer from the total mass of said composition, said composition comprises between about 8 g/kg and about 40 g/kg of L-cystine.
31. The composition of embodiment 30, wherein, excluding said phosphate buffer from the total mass of said composition, said composition comprises between about 12 g/kg and about 20 g/kg of L-cystine.
32. The composition of embodiment 31, wherein, excluding said phosphate buffer from the total mass of said composition, said composition comprises about 17.5 g/kg of L-cystine.
33. The composition of any one of embodiments 2 to 32, wherein said composition further comprises a gelling agent.
34. The composition of embodiment 33, wherein said gelling agent is selected from the group consisting of agar, gellan, sodium alginate, xanthan gum, guar gum, gelatin, agarose, and a polysaccharide produced by *Rhizobium* sp. (CNCM number: I-1809).
35. The composition of embodiment 34, wherein said gelling agent is agar.
36. The composition of any one of embodiments 33 to 35, wherein said composition comprises between about 10 g/kg and about 800 g/kg of said gelling agent.
37. The composition of embodiment 36, wherein said composition comprises between about 100 g/kg and about 600 g/kg of said gelling agent.
38. The composition of embodiment 37, wherein said composition comprises between about 250 g/kg and about 450 g/kg of said gelling agent
39. The composition of embodiment 38, wherein said composition comprises about 350 g/kg of said gelling agent.

40. The composition of any one of embodiments 2 to 39, wherein said composition further comprises a surfactant.
41. The composition of embodiment 40, wherein said surfactant is a polysorbate.
42. The composition of embodiment 40 or 41, wherein said composition comprises between about 0.4 g/kg and about 190 g/kg of said surfactant.
43. The composition of embodiment 42, wherein said composition comprises between about 4 g/kg and about 80 g/kg of said surfactant.
44. The composition of embodiment 43, wherein said composition comprises between about 4 g/kg and about 40 g/kg of said surfactant.
45. The composition of embodiment 44, wherein said composition comprises about 20 g/kg of said surfactant.
46. The composition of embodiment 1, wherein, at 22° C., said composition is a liquid or a gel.
47. The composition of embodiment 1 or 46 further comprising purified water.
48. The composition of any one of embodiments 1, 46, and 47, further comprising sheep blood.
49. The composition of embodiment 48, wherein the concentration of said sheep blood in said composition is between about 5 mL/kg and about 200 mL/kg.
50. The composition of embodiment 49, wherein the concentration of said sheep blood in said composition is between about 5 mL/kg about 100 mL/kg.
51. The composition of embodiment 50, wherein the concentration of said sheep blood in said composition is about 50 mL/kg.
52. The composition of any one of embodiments 48 to 51, wherein red blood cells in said sheep blood are lysed.
53. The composition of any one of embodiments 48 to 52, wherein said sheep blood is laked sheep blood.
54. The composition of any one of embodiments 48 to 52, wherein said sheep blood is defibrinated sheep blood.
55. The composition of any one of embodiments 46 to 54, wherein the concentration of casein digest in said composition is between about 0.1 g/kg and about 50 g/kg.
56. The composition of embodiment 55, wherein the concentration of casein digest in said composition is between about 1 g/kg and about 20 g/kg.
57. The composition of embodiment 56, wherein the concentration of casein digest in said composition is between about 2 g/kg and about 10 g/kg.
58. The composition of embodiment 57, wherein the concentration of casein digest in said composition is about 5.6 g/kg.
59. The composition of any one of embodiments 46 to 58, wherein the concentration of soybean digest in said composition is between about 0.05 g/kg and about 30 g/kg.
60. The composition of embodiment 59, wherein the concentration of soybean digest in said composition is between about 0.1 g/kg and about 10 g/kg.
61. The composition of embodiment 60, wherein the concentration of soybean digest in said composition is between about 0.2 g/kg and about 3 g/kg.
62. The composition of embodiment 61, wherein the concentration of soybean digest in said composition is about 1 g/kg.
63. The composition of any one of embodiments 46 to 62, wherein the concentration of animal tissue digest in said composition is between about 0.1 g/kg and about 50 g/kg.
64. The composition of embodiment 63, wherein the concentration of animal tissue digest in said composition is between about 1 g/kg and about 20 g/kg.
65. The composition of embodiment 64, wherein the concentration of animal tissue digest in said composition is between about 2 g/kg and about 10 g/kg.
66. The composition of embodiment 65, wherein the concentration of animal tissue digest in said composition is about 5 g/kg.
67. The composition of any one of embodiments 46 to 66, wherein the concentration of yeast extract in said composition is between about 0.1 g/kg and about 50 g/kg.
68. The composition of embodiment 67, wherein the concentration of yeast extract in said composition is between about 1 g/kg and about 20 g/kg.
69. The composition of embodiment 68, wherein the concentration of yeast extract in said composition is between about 2 g/kg and about 10 g/kg.
70. The composition of embodiment 69, wherein the concentration of yeast extract in said composition is about 5 g/kg.
71. The composition of any one of embodiments 46 to 70, wherein the concentration of dextrose in said composition is between about 0.1 g/kg and about 50 g/kg.
72. The composition of embodiment 71, wherein the concentration of dextrose in said composition is between about 1 g/kg and about 20 g/kg.
73. The composition of embodiment 72, wherein the concentration of dextrose in said composition is between about 2 g/kg and about 10 g/kg.
74. The composition of embodiment 73, wherein the concentration of dextrose in said composition is 5.8 g/kg.
75. The composition of any one of embodiments 46 to 74, wherein said composition comprises a quantity of phosphate buffer sufficient to provide a buffer capacity of from 0.1 mmol/(pH unit) to 100 mmol/pH.
76. The composition of embodiment 75, wherein said composition comprises a quantity of phosphate buffer sufficient to provide a buffer capacity of from 1 mmol/(pH unit) to 50 mmol/(pH unit) upon dissolution in an aqueous medium.
77. The composition of embodiment 76, wherein said composition comprises a quantity of phosphate buffer sufficient to provide a buffer capacity of from 2 mmol/(pH unit) to 20 mmol/(pH unit) upon dissolution in an aqueous medium.
78. The composition of embodiment 77, wherein said composition comprises a quantity of phosphate buffer sufficient to provide a buffer capacity of from 3 mmol/(pH unit) to 10 mmol/(pH unit) upon dissolution in an aqueous medium.
79. The composition of any one of embodiments 46 to 78, wherein the concentration of hemin in said composition is about 0.01 g/kg.
80. The composition of any one of embodiments 46 to 79, wherein the concentration of L-cystine in said composition is between about 0.01 g/kg and about 0.5 g/kg.
81. The composition of embodiment 80, wherein the concentration of L-cystine in said composition is about 0.4 g/kg.

82. The composition of any one of embodiments 46 to 81 further comprising a surfactant.
83. The composition of embodiment 82, wherein said surfactant is a polysorbate.
84. The composition of embodiment 83, wherein said composition comprises between about 0.01 g/kg and about 5 g/kg of said surfactant.
85. The composition of embodiment 84, wherein said composition comprises between about 0.1 g/kg and about 2 g/kg of said surfactant.
86. The composition of embodiment 85, wherein said composition comprises between about 0.1 g/kg and about 1 g/kg of said surfactant.
87. The composition of embodiment 86, wherein said composition comprises about 0.5 g/kg of said surfactant.
88. The composition of any one of embodiments 46 to 87 further comprising a gelling agent.
89. The composition of embodiment 88, wherein said gelling agent is selected from the group consisting of agar, gellan, sodium alginate, xanthan gum, guar gum, gelatin, agarose, polyacrylamide, and a polysaccharide produced by *Rhizobium* sp. (CNCM number: I-1809).
90. The composition of embodiment 89, wherein said gelling agent is agar.
91. The composition of embodiment 90, wherein said gelling agent is a polysaccharide produced by *Rhizobium* sp.
92. The composition of embodiment 90 or 91, wherein the concentration of said gelling agent in said composition is between about 5 g/kg and about 25 g/kg.
93. The composition of embodiment 92, wherein the concentration of said gelling agent in said composition is about 13.5 g/kg.
94. The composition of embodiment 93, wherein said gelling agent is gellan.
95. The composition of embodiment 94, wherein the concentration of gellan in said composition is between about 1.0 g/kg and about 13 g/kg.
96. The composition of embodiment 95, wherein the concentration of gellan in said composition is about 6.8 g/kg.
97. The composition of embodiment 89, wherein said gelling agent is xanthan gum or sodium alginate.
98. The composition of embodiment 97, wherein the concentration of said gelling agent in said composition is between about 3.4 g/kg and about 17 g/kg.
99. The composition of embodiment 98, wherein the concentration of said gelling agent in said composition is about 9 g/kg.
100. The composition of embodiment 89, wherein said gelling agent is polyacrylamide.
101. The composition of embodiment 100, wherein the concentration of polyacrylamide in said composition is between about 50 g/kg and about 200 g/kg.
102. The composition of embodiment 101, wherein the concentration of polyacrylamide in said composition is about 150 g/kg.
103. The composition of embodiment 89, wherein said gelling agent is guar gum.
104. The composition of embodiment 103, wherein the concentration of guar gum in said composition is between about 10 g/kg and about 40 g/kg.
105. The composition of embodiment 104, wherein the concentration of guar gum in said composition is about 21 g/kg.
106. The composition of any one of embodiments 46 to 87, wherein said composition is a liquid.
107. The composition of any one of embodiments 46 to 105, wherein said composition is a gel.
108. The composition of any one of embodiments 1 and 46-107, wherein said composition has a pH of 7.3±0.5.
109. The composition of any one of embodiments 1 to 108, wherein said composition does not comprise tris(hydroxymethyl)aminomethane.
110. The composition of any one of embodiments 1 to 109, wherein said composition does not contain added sodium.
111. A method of culturing a population of cells comprising contacting said population of cells with the composition of any one of embodiments 46 to 110 under conditions supportive of growth of said population of cells.
112. The method of embodiment 111, wherein said population of cells is disposed on a first side of a membrane, and a second side of said membrane is in contact with the composition of any one of embodiments 46 to 110.
113. The method of embodiment 112, wherein said membrane is permeable.
114. The method of any one of embodiments 111 to 113, wherein one or more cells within said population of cells are aerobes.
115. The method of any one of embodiments 111 to 113, wherein one or more cells within said population of cells are anaerobes.
116. The method of embodiment 115, wherein said anaerobe is an obligate anaerobe.
117. The method of any one of embodiments 111 to 113, wherein one or more cells within said population of cells belong to a genus selected from the group consisting of *Acinetobacter, Aspergillus, Bacillus, Corynebacterium, Dermacoccus, Escherichia, Exserohilum, Kocuria, Methylobacterium, Micrococcus, Paenibacillus, Penicillium, Propionibacterium, Pseudomonas, Staphylococcus, Streptococcus,* and *Streptomyces.*
118. The method of embodiment 117, wherein said *Staphylococcus* is *Staphylococcus aureus, Staphylococcus epidermidis,* or *Staphylococcus hominis.*
119. The method of embodiment 117, wherein said *Methylobacterium* is *Methylobacterium radiotolerans.*
120. The method of embodiment 117, wherein said *Bacillus* is *Bacillus clausii, Bacillus idriensis, Bacillus licheniformis,* or *Bacillus substilis.*
121. The method of embodiment 117 or 120, wherein said *Bacillus* is oxidatively stressed.
122. The method of embodiment 117, wherein said *Aspergillus* is *Aspergillus brasiliensis* or *Aspergillus fumigatus.*
123. The method of embodiment 117, wherein said *Corynebacterium* is *Corynebacterium tuberculostearicum* or *Corynebacterium xerosis.*
124. The method of embodiment 117, wherein said *Dermacoccus* is *Dermacoccus nishinomiyaensis.*
125. The method of embodiment 117, wherein said *Escherichia* is *Escherichia coli.*
126. The method of embodiment 117, wherein said *Kocuria* is *Kocuria rhizophila.*
127. The method of embodiment 117, wherein said *Micrococcus* is *Micrococcus luteus.*
128. The method of embodiment 117, wherein said *Paenibacillus* is *Paenibacillus glucanolyticus.*

129. The method of embodiment 117, wherein said *Penicillium* is *Penicillium chrysogenum* or *Penicillium notatum*.
130. The method of embodiment 117, wherein said *Pseudomonas* is *Pseudomonas aeruginosa*.
131. The method of embodiment 117, wherein said *Streptococcus* is *Streptococcus pyogenes*.
132. The method of embodiment 117, wherein said *Streptomyces* is *Streptomyces halstedii*. 133. The method of embodiment 117, wherein said *Acinetobacter* is *Acinetobacter lwofii*.
134. The method of embodiment 117, wherein said *Propionibacterium* is *Propionibacterium acnes*.
135. The method of embodiment 117, wherein said *Exserohilum* is *Exserohilum rostratum*.
136. The method of any one of embodiments 111 to 135, wherein said population of cells is from a sample.
137. The method of embodiment 136, wherein said sample comprises fluids or tissues obtained from a multicellular organism.
138. The method of embodiment 137, wherein said sample comprises the bodily fluids or tissues of an animal.
139. The method of embodiment 138, wherein said sample is derived from a human.
140. The method of embodiment 138, wherein said sample is derived from a non-human vertebrate.
141. The method of any one of embodiments 137 to 140, wherein said sample is selected from the group consisting of: respiratory, urogenital, reproductive tract, central nervous system, urine, blood, dermal, plasma, serum, saliva, wound tissue, wound exudate, biopsy, feces, reproductive tract, and solid tissue samples, and derivatives thereof.
142. The method of embodiment 141, wherein said sample is a blood or urine sample.
143. The method of embodiment 137, wherein said sample is derived from a plant.
144. The method of any one of embodiments 136 to 143, wherein said sample is obtained by sampling environmental air, soil, or water, or surfaces, objects, or organisms exposed to the environment.
145. The method of embodiment 136, wherein said sample is obtained from a material selected from the group consisting of raw, finished, or in-process material in the manufacture of pharmacological, cosmetic, blood, or other products for topical or internal use in humans or animals; raw, in-process, or finished material in the manufacture of foods, beverages, or nutritional supplements; raw, in-process, or finished material in the manufacture of medical or in vitro diagnostic devices; chemical products; industrial surfaces; instrumentation; and machinery.
146. The method of any one of embodiments 136 to 145, wherein said sample is treated to liquefy and/or homogenize it prior to said contacting.
147. The method of any one of embodiments 136 to 146, wherein said sample is treated to remove substances or objects other than said population of cells prior to said contacting.
148. A method of preparing the composition of any one of embodiments 46 to 110 comprising:
  i) autoclaving a mixture comprising purified water, casein digest, soybean digest, a phosphate buffer, dextrose, animal tissue digest, yeast extract, hemin, and L-cystine;
  ii) optionally cooling said mixture;
  iii) optionally adjusting pH to 7.3±0.5 by adding sterile potassium hydroxide or hydrogen chloride to said mixture; and
  iv) adding sheep blood to said mixture.
149. The method of embodiment 148, further comprising vi) holding the temperature of said mixture at about 65° C. until the color of said mixture changes from red to brown.
150. The method of embodiment 148 or 149, wherein said cooling in step ii) is cooling to room temperature.
151. The method of embodiment 148 or 149, wherein said cooling in step ii) is cooling to about 42° C.
152. The method of any one of embodiments 148 to 151, wherein said mixture of step i) further comprises a gelling agent.
153. The method of any one of embodiments 148 to 152, wherein said mixture of step i) further comprises a surfactant.
154. The method of any one of embodiments 148 to 152 further comprising adding a surfactant to said mixture after step i).
155. The method of embodiment 153 or 154, wherein said surfactant is a polysorbate.
156. The method of any one of embodiments 153 to 155, wherein said surfactant is provided as an aqueous solution comprising 5% (w/v) of said surfactant.
157. The method of any one of embodiments 148 to 156 further comprising transferring said composition into a storage vessel after preparation steps are complete.
158. The method of embodiment 157, wherein said storage vessel is a bottle, a jar, a vial, an ampoule, or a cassette.
159. The method of embodiment 157 or 158 further comprising γ-irradiating said storage vessel after said transferring.
160. The method of embodiment 159, wherein the dosage of said γ-irradiating is greater than 10 kGy.
161. The method of embodiment 160, wherein the dosage of said γ-irradiating is between about 10 kGy and about 50 kGy.
162. The method of embodiment 161, wherein the dosage of said γ-irradiating is between about 10 kGy and about 40 kGy.
163. The method of embodiment 162, wherein the dosage of said γ-irradiating is between about 10 kGy and about 20 kGy.
164. The method of embodiment 163, wherein the dosage of said γ-irradiating is between about 12 kGy and about 19 kGy.
165. The composition or method of any of embodiments 1 to 164, wherein the composition further comprises a disinfectant neutralizer.
166. The composition or method of embodiment 165, wherein the neutralizer is histidine, thiosulfate, polysorbate 80, and/or lecithin.

OTHER EMBODIMENTS

Various modifications and variations of the described composition and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A composition comprising casein digest, soybean digest, animal tissue digest, yeast extract, dextrose, a phosphate buffer, hemin, and L-cystine, wherein said composition does not comprise tris(hydroxymethyl)aminomethane, wherein, at 22° C., said composition is solid, and, excluding said phosphate buffer from the total mass of said composition, said composition comprises between about 1 g/kg and about 500 g/kg of casein digest; between about 0.5 g/kg and about 300 g/kg of soybean digest; between about 1 g/kg and about 500 g/kg of animal tissue digest; between about 1 g/kg and about 500 g/kg of yeast extract; between about 1 g/kg and about 500 g/kg of dextrose; and between about 8 g/kg and about 40 g/kg of L-cystine.

2. The composition of claim 1, wherein said composition is a powder.

3. The composition of claim 1, wherein said composition comprises a quantity of phosphate buffer sufficient to provide a buffer capacity of from 0.1 mmol/(pH unit) to 100 mmol/(pH unit) upon dissolution in an aqueous medium.

4. The composition of claim 1, wherein said composition comprises between about 0.2 g/kg and about 1 g/kg of hemin.

5. The composition of claim 1, wherein said composition further comprises a surfactant.

6. The composition of claim 5, wherein said surfactant is a polysorbate.

7. A composition comprising casein digest, soybean digest, animal tissue digest, yeast extract, dextrose, a phosphate buffer, hemin, and L-cystine, wherein said composition does not comprise tris(hydroxymethyl)aminomethane, wherein, at 22° C., said composition is a liquid or a gel and wherein the concentration of casein digest in said composition is between about 0.1 g/kg and about 50 g/kg; the concentration of soybean digest in said composition is between about 0.05 g/kg and about 30 g/kg; the concentration of animal tissue digest in said composition is between about 0.1 g/kg and about 50 g/kg; the concentration of yeast extract in said composition is between about 0.1 g/kg and about 50 g/kg; the concentration of dextrose in said composition is between about 0.1 g/kg and about 50 g/kg and the concentration of L-cystine in said composition is between about 0.01 g/kg and about 0.5 g/kg.

8. The composition of claim 7 further comprising purified water.

9. The composition of claim 7, further comprising sheep blood.

10. The composition of claim 9, wherein the concentration of said sheep blood in said composition is between about 5 mL/kg and about 200 mL/kg.

11. The composition of claim 9, wherein said sheep blood is laked sheep blood.

12. The composition of claim 7, wherein said composition comprises a quantity of phosphate buffer sufficient to provide a buffer capacity of from 0.1 mmol/(pH unit) to 100 mmol/(pH unit).

13. The composition of claim 7, wherein the concentration of hemin in said composition is about 0.01 g/kg.

14. The composition of claim 7, further comprising a surfactant.

15. The composition of claim 14, wherein said surfactant is a polysorbate.

16. The composition of claim 7, further comprising a gelling agent.

17. The composition of claim 16, wherein said gelling agent is selected from the group consisting of agar, gellan, sodium alginate, xanthan gum, guar gum, gelatin, agarose, polyacrylamide, and a polysaccharide produced by *Rhizobium* sp. (CNCM number: I-1809).

18. The composition of claim 17, wherein said gelling agent is agar.

19. The composition of claim 17, wherein the concentration of said gelling agent in said composition is between about 10 g/kg and about 800 g/kg of said gelling agent for a solid and between about 5 g/kg and about 25 g/kg for a liquid or gel.

20. The composition of claim 7, wherein said composition has a pH of 7.3±0.5.

21. The composition of claim 1, wherein said composition does not contain added sodium.

22. The composition of claim 1, further comprising a disinfectant neutralizer.

23. The composition of claim 22, wherein said neutralizer is histidine, thiosulfate, polysorbate 80, and/or lecithin.

24. A method of culturing a population of cells comprising contacting said population of cells with the composition of claim 7 under conditions supportive of growth of said population of cells.

25. The method of claim 24, wherein said population of cells is disposed on a first side of a membrane, and a second side of said membrane is in contact with the composition.

26. The method of claim 24, wherein one or more cells within said population of cells are aerobes.

27. The method of claim 24, wherein one or more cells within said population of cells are anaerobes.

28. The method of claim 24, wherein one or more cells within said population of cells belong to a genus selected from the group consisting of *Acinetobacter, Aspergillus, Bacillus, Corynebacterium, Dermacoccus, Escherichia, Exserohilum, Kocuria, Methylobacterium, Micrococcus, Paenibacillus, Penicillium, Propionibacterium, Pseudomonas, Staphylococcus, Streptococcus*, and *Streptomyces*.

29. A method of preparing the composition of claim 7 comprising:
   i) autoclaving a mixture comprising purified water, casein digest, soybean digest, a phosphate buffer, dextrose, animal tissue digest, yeast extract, hemin, and L-cystine;
   ii) optionally cooling said mixture;
   iii) optionally adjusting pH to 7.3±0.5 by adding sterile potassium hydroxide or hydrogen chloride to said mixture; and
   iv) adding sheep blood to said mixture.

30. The method of claim 29, further comprising vi) holding the temperature of said mixture at about 65° C. until the color of said mixture changes from red to brown.

31. The method of claim 29, wherein said cooling in step ii) is cooling to room temperature.

32. The method of claim 29, wherein said mixture of step i) further comprises a gelling agent.

33. The method of claim 29, wherein said mixture of step i) further comprises a surfactant.

* * * * *

UNITED STATES PATENT AND TRADEMARK OFFICE
CERTIFICATE OF CORRECTION

| | |
|---|---|
| PATENT NO. | : 10,793,823 B2 |
| APPLICATION NO. | : 15/305789 |
| DATED | : October 6, 2020 |
| INVENTOR(S) | : Shara et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 510 days.

Signed and Sealed this
Twentieth Day of December, 2022

*Katherine Kelly Vidal*

Katherine Kelly Vidal
*Director of the United States Patent and Trademark Office*